US005585351A

United States Patent [19]
Ranscht

[11] Patent Number: 5,585,351
[45] Date of Patent: Dec. 17, 1996

[54] T-CADHERIN ADHESION MOLECULE

[75] Inventor: Barbara Ranscht, Del Mar, Calif.

[73] Assignee: La Jolla Cancer Research Foundation, La Jolla, Calif.

[21] Appl. No.: 213,361

[22] Filed: Mar. 14, 1994

Related U.S. Application Data

[63] Continuation of Ser. No. 607,293, Oct. 30, 1990, abandoned.
[51] Int. Cl.⁶ ................................................ A61K 38/00
[52] U.S. Cl. .......................... 514/12; 530/395; 530/399; 530/324
[58] Field of Search .................................. 530/395, 399, 530/324

[56] References Cited

PUBLICATIONS

Neugehauer et al., Chem. Abst., 109, 487, 1988, abst No. 109:167903c.
Laemmli, Nature, 227, 680–685, 1970.
Ranscht et al., J. Cell Biol., 99, 1803–18113, 1984.
Ozawa et al., Single amino acid substitutions in one $Ca^{2+}$ binding site of uvomorulin abolish the adhesive function. Cell 63:1033–1038 (1990).
Takeuchi, Cadherins: a molecular family important in selective cell–cell adhesion. Annu. Rev. Biochem. 59:237–252 (1990).
Ranscht, Cadherin cell adhesion molecules in vertebrate neural development. Seminars in the Neurosciences 3:285–296 (1991).
Ranscht and Dours–Zimmerman, T–cadherin, a novel cadherin cell adhesion molecule in the nervous system lacks the conserved cytoplasmic region. Neuron 7:391–402 (1991).
Laemmli, Cleavage of structural proteins during the assembly of the head of bacteriophage T4. Nature 227:680–685 (1970).
Ranscht et al., A neuronal surface glycoprotein associated with the cytoskeleton. J. Cell Biol. 99:1803–1813 (1984).
Edelman et al., Cellular expression of liver and neural cell adhesion molecules after transfection with their cDNAs results in specific cell–cell binding. Proc. Natl. Acad. Sci. USA 84:8502–8506 (1987).
Gallin et al., Sequence analysis of a cDNA clone encoding the liver cell adhesion molecule, L–CAM. Proc. Natl. Acad. Sci. USA 84:2808–2812 (1987).
Hatta et al., Spatial and Temporal Expression Pattern of N–cadherin cell adhesion molecules correlated with morphogenetic processes of chicken embryos. Dev. Biol. 120:215–217 (1987).
Nagafuchi et al., Transformation of cell adhesion properties by exogenously introduced E–cadherin cDNA. Nature 329:341–343 (1987).
Nose et al., Isolation of placental cadherin cDNA: Identification of a novel gene family of cell–cell adhesion molecules. EMBO J. 6(12):3655–3661 (1987).
Ringwald et al., The structure of cell adhesion molecule uvomorulin. Insights into the molecular mechanism of $Ca^{2+}$–dependent cell adhesion. EMBO J. 6(12):3647 (1987).

Hatta et al., Cloning and expression of cDNA encoding a neural calcium–dependent cell adhesion molecule: Its identity in the cadherin gene family, J. Cell. Biol. 106:873–881 (1988).
Mege et al., Construction of epithelioid sheets by transfection of mouse sarcoma cells with cDNAs for chicken cell adhesion molecules. Proc. Natl. Acad. Sci. USA 85:7274–7278 (1988).
Nagafuchi and Takeichi, Cell binding function of E–cadherin is regulated by the cytoplasmic domain. EMBO J. 7(12):3679–3684 (1988).
Neugebauer et al., N–cadherin, NCAM, and integrins promote retinal neurite outgrowth on astrocytes in vitro. Chem. Abstract 109:487, abstract No. 109:167903c (1988).
Takeichi, The cadherins: cell–cell adhesion molecules controlling animal morphogenesis. Development 102:639–655 (1988).
Kemler and Ozawa, Uvomorulin–catenin complex: cytoplasmic anchorage of a $Ca^{2+}$–dependent cell adhesion molecule. BioEssays 11(4):88–91 (1989).
Moss and White, A $Ca^{2+}$–sensitive glycoprotein. GP90, associated with the cytoskeleton from brain and gizzard, J. Cell. Sci. 93:85–94 (1989).
Nagafuchi and Takeichi, Transmembrane control of cadherin–mediated cell adhesion: a 94 kDa protein functionally associated with a specific region of the cytoplasmic domain of E–cadherin. Cell Regulation 1:37–44 (1989).
Ozawa et al., The cytoplasmic domain of the cell adhesion molecule uvomorulin associates with three independent proteins structurally related in different species. EMBO J. 8(6):1711–1717 (1989).
Rancht and Dours, Selective Expression of a novel cadherin in the pathways of developing motor and commissural axons. Society for Neuroscience Abstracts 15(part 1), abstract No. 382.6 (1989).
Bixby and Zhang, Purified N–cadherin is a potent substrate for the rapid induction of neurite outgrowth. J. Cell Biol. 110:1253–1260 (1990).
Matsuzaki et al., DNAs of cell adhesion molecules of different specificity induce changes in cell shape and border formation in cultured S180 cells. J. Cell. Biol. 110:1239–1252 (1990).

(List continued on next page.)

Primary Examiner—Jill Warden
Assistant Examiner—Benet Prickril
Attorney, Agent, or Firm—Campbell and Flores

[57] ABSTRACT

The invention provides substantially purified T-cadherin polypeptides and isolated nucleic acids which encode the T-cadherin polypeptides. Antibodies reactive with various forms of T-cadherin, but not reactive with N-, E- or P-cadherin are also provided. The invention provides methods for detecting the various forms of T-cadherin in a subject as well as a method of detecting tumor growth which consists of inhibiting the activity of T-cadherin in a tumor. A method of effecting traumatized neurons is provided. The method entails treating traumatized neurons with a therapeutically effective dose of T-cadherin.

4 Claims, 19 Drawing Sheets

PUBLICATIONS

McNeill et al., Novel function of the cell adhesion molecule uvomorulin as an inducer of cell surface polarity. Cell 62:309–316 (1990).

Nose et al., Localization of specificity determining sites in cadherin cell adhesion molecules. Cell 61:147–155 (1990).

Ozawa et al., Uvomorulin–catenin complex formation is regulated by a specific domain in the cytoplasmic region of the cell adhesion molecule. Proc. Natl. Acad. Sci. USA 87:4246–4250 (1990).

Ozawa and Kemler, Correct proteolytic cleavage is required for the cell adhesive function of uvomorulin. J. Cell. Biol. 111:1645–1650 (1990).

```
      GAATTCCGAATGAAAAAGCCTCTCGGTACGTTCTAGTCTGGCAAAATGCAGCACAAAACTCAACTTACTCTGTCCTTTCTGCTGTCCCAG
  1
                                                     M   Q   H   K   T   Q   L   T   L   S   F   L   L   S   Q
 -22

GTTCTGTTGCTTGCTGTGCAGAAGATTTAGAATGCACCCCTGATTCCAGCAAAAGGTTTTTTATATTGAACAGCCATTTGAATTCACA
 90    V   L   L   A   C   A   E   D   L   E   C   T   P   G   F   Q   Q   K   V   F   Y   I   E   Q   P   F   E   F   T
 -7

GAGGACCAGCCAATTCTGAACCTGGTGTTTGATGACTGCAAGGGGAATAACAAATTGAACTTCGAAGTTTCTAACCCAGACTTTAAGGTG
180    E   D   Q   P   I   L   N   L   V   F   D   D   C   K   G   N   N   K   L   N   F   E   V   S   N   P   D   F   K   V
 24

GAACACGATGGATCTTTAGTTGCACTGAAAGAATGTATCAGAAGCTTGTTTGTTCCATGCACGGTCTGACGATGCTGAGGAT
270    E   H   D   G   S   L   V   A   L   K   N   V   S   E   A   G   R   A   L   F   V   H   A   R   S   E   H   A   E   D
 54

ATGGCAGAAATTTGATTGTTGGAGCTGATGAGAAGCACGATGCATTAAAGGAAATCTTTAAGATAGAAGGCAACCTTGGAATTCCAAGA
360    M   A   E   I   L   I   V   G   A   D   E   K   H   D   A   L   K   E   I   F   K   I   E   G   N   L   G   I   P   R
 84

CAAAAAGGGCTATTCTGGCGACTCCAATATTAATTCCAGAAAATCAAAGACCCATTCCCAGATCAGTTGGCAAGGTCATCAGGAGT
450    Q   K   R   A   I   L   A   T   P   I   L   I   P   E   N   Q   R   P   P   F   P   R   S   V   G   K   V   I   R   S
114

GAAGGGACAGAGGAGCAAAGTTCCGACTCTCTCGGTAAGGGAGTAGATCAAGACCCGAAAGGAATTTTAGAATCAATGAGATCAGTGGG
540    E   G   T   E   G   A   K   F   R   L   S   G   K   G   V   D   Q   D   P   K   G   I   F   R   I   N   E   I   S   G
144

GATGTCTCTGTGACCCGACCCCTGGATAGAGAAGCCAATAGCCAATTATGAGCTGGAAGTTGAAGTAACGGATTTAAGTGGGAAAATCATT
630    D   V   S   V   T   R   P   L   D   R   E   A   I   A   N   Y   E   L   E   V   E   V   T   D   L   S   G   K   I   I
174

GATGGCCCAGTCCGCTTAGATATTTCTGTTATTGATCAAAATGATAACAGGCCGATGTTCAAAGAAGGACCCTATGTTGTCACGTCATG
720    D   G   P   V   R   L   D   I   S   V   I   D   Q   N   D   N   R   P   M   F   K   E   G   P   Y   V   V   G   H   V   M
204

GAAGGATCCCCTACAGGAACACTTGATGCGGATGACAGCATTTGATGCTGATGATCCTAGCACAGATGATGCTGATGATCCTAGCACAGATAATGCTCTTCTGCGTATAAC
810    E   G   S   P   T   G   T   T   V   M   R   M   T   A   F   D   A   D   D   P   S   T   D   N   A   L   L   R   Y   N
234

ATCCTCAAGCAGACAGACACCTTCCCCAAATGTTCTACATTGACCCAGAAAAGGGAGATATTGTCACAGTGGTGTCACCTGTA
900    I   L   K   Q   T   P   T   K   P   S   P   N   M   F   Y   I   D   P   E   K   G   D   I   V   T   V   V   S   P   V
264

CTGCTGGATCGTGAGACAATGGAAACGCCGAAGTACGAGCTGGTTATTGAAGCCAAGGATATGGGCGGCCATGATGTGGGGACTTACTGGA
990    L   D   R   E   T   M   E   T   P   K   Y   E   L   V   I   E   A   K   D   M   G   G   H   D   V   G   L   T   G
294
```

FIG.2A

```
1080  ACTGCAACTGCCACTATTCTTATTGATGACAAAACGACCACCCAGAATTTACCAAGAAGAAGTTTCAGGCCACAGTAAAGGAAGGA
 324   T  A  T  I  L  L  I  D  D  K  N  D  H  P  P  E  F  T  K  K  E  F  Q  A  T  V  K  E  G

1170  GTCACAGGAGTAATAGTAAACTTAACTGTTGGTGACCGAGATGACCCAGCAACTGGAGCATGGAGACTGTCTACACTATTATAACGGA
 354   V  T  G  V  I  V  N  L  T  V  G  D  R  D  D  P  A  T  G  A  W  R  A  V  Y  T  I  I  N  G

1260  AATCCAGGGCAGAGTTTTGAAATCCATACCAATCCCCAGACTAATGAGGGAATGCTCTCTGTTGTCAAACCTTTAGACTATGAGATTCA
 384   N  P  G  Q  S  F  E  I  H  T  N  P  Q  T  N  E  G  M  L  S  V  V  K  P  L  D  Y  E  I  S

1350  GCATTCACACATTGCTGATAAAGTAGAAAATGAAGACCCGTTGATTCCAGACATAGCCTACGGTCCCAGTTCCACAGCAACAGTTCAG
 414   A  F  H  T  L  L  I  K  V  E  N  E  D  P  L  I  P  D  I  A  Y  G  P  S  S  T  A  T  V  Q

1440  ATCACCGTTGAGGATGTGAATGAAGGCCCTGTTTTCCACCCAAATCCAATGACAGTGACAAAACAAGAGAACATCCCTATTGGCAGCATT
 444   I  T  V  E  D  V  N  E  G  P  V  F  H  P  N  P  M  T  V  T  K  Q  E  N  I  P  I  G  S  I

1530  GTGTTAACAGTAAATGCCACTGATCCAGATACTTTGCAACATCAGATTCAGTTATTCAGTTATCGATATCGGGAATCTCCTCATGTTCAAGATAACAAATACACTGCTCTCTTC
 474   V  L  T  V  N  A  T  D  P  D  T  L  Q  H  Q  T  I  R  Y  S  V  Y  K  D  P  A  S  W  L  E

1620  ATTAATCCCACCAATGGTACCGTTGCCACCACTGCTGTCCTGGATCGGGAATCTCCTCATGTTCAAGATAACAAATACACTGCTCTCTTC
 504   I  N  P  T  N  G  T  V  A  T  T  A  V  L  D  R  E  S  P  H  V  Q  D  N  K  Y  T  A  L  F

1710  CTGGCAATAGACAGTGGTAACCCTCCTGCTACAGGAACTTTACACATCACCTTGCATATCACCTTGGAGGACGTCAATGACAATGTCCCCTCCTT
 534   L  A  I  D  S  G  N  P  P  A  T  G  T  L  H  I  T  L  E  D  V  N  D  N  V  P  S  L

1800  TACCCAACACTGGCAAAAGTCTGTGATGATGCTAAAGATCTGAGAGTAGTGGTACTAGGAGCATCAGACAAAGACCTCCATCCAACACA
 564   Y  P  T  L  A  K  V  C  D  D  A  K  D  L  R  V  V  L  G  A  S  D  K  D  L  H  P  N  T

1890  GATCCATTTAAATTTGAACTGAGTAAGCAATCTGGTCCAGAAAAGTTATGGAGAATCAACAAGCTTAACAATACTCATGCCCAGGTTGTC
 594   D  P  F  K  F  E  L  S  K  Q  S  G  P  E  K  L  W  R  I  N  K  L  N  N  T  H  A  Q  V  V

1980  CTGCTTCAAAACCTGAAAAAGGCCAATTACAACATCCCAATCTCAGTGACAGATTCTGAAAAACCACCTCTGACTAACAACAGAACTG
 624   L  L  Q  N  L  K  K  A  N  Y  N  I  P  I  S  V  T  D  S  G  K  P  P  L  T  N  N  T  E  L
```

```
  1  GAATTCCAAAAGCCTCTGGTACGTTCTAGTCTCTGGCAAATGCAGCACAAACTCAACTTACTCTGTCCTTCTGCTGTCCCAGTTCTG
-22                                            M  Q  H  K  T  Q  L  T  L  S  F  L  L  S  Q  V  L

91  TTGCTTGCCGTGTGCAGAAGATTAGAATGCACCCCCTGGATTCCAGCAAAAGTTTTTTATATTGAACAGCCATTTGAATTCACAGAGGAC
 -5   L  L  A  C  A  E  D  L  E  C  T  P  G  F  Q  Q  K  V  F  Y  I  E  Q  P  F  E  F  T  E  D

181  CAGCCAATTCTGAACCTGGTGTTTGATGACTGCAAGGGGAATAACAAATTGAACTTCGAAGTTCTAACCCAGACTTTAAGGTGGAACAC
 26   Q  P  I  L  N  L  V  F  D  D  C  K  G  N  N  K  L  N  F  E  V  S  N  P  D  F  K  V  E  H

271  GATGGATCTTTAGTGCACTGAAGAATGTATCAGAAGCTGGCAGCACGGTCTGAGCATGCTGAGGATATGGCA
 56   D  G  S  L  V  A  L  K  N  V  S  E  A  G  R  A  L  F  V  H  A  R  S  E  H  A  E  D  M  A

361  GAAATTTGATTGTGGAGCTGATGAGAAGCACGATGCATTAAGAAGCAACCTTGGAATTCCAAGACAAAAA
 86   E  I  L  I  V  G  A  D  E  K  H  D  A  L  K  E  I  F  K  I  E  G  N  L  G  I  P  R  Q  K

451  AGGGCTATTCTGGCGACTCCAATATTAATTCCAGAAAATCAAAGACCACCATTCCCAGATCAGTTGGCAAGTCATCAGGAGTGAAGG
116   R  A  I  L  A  T  P  I  L  I  P  E  N  Q  R  P  P  P  R  S  V  G  K  V  I  R  S  E  G

541  ACAGAGGGAGCAAAGTTCGACTCTCTGGTAAGGGAGTAGATCAAGGAATTTTAGAATCAATGAGATCAGTGGGATGTC
146   T  E  G  A  K  F  R  L  S  G  K  G  V  D  Q  D  P  K  G  I  F  R  I  N  E  I  S  G  D  V

631  TCTGTGACCCGACCCCTAGATAGAGAAGCAATTGCCAATTATGAGTTGAAGTAACGGATTTAAGTGGAAAATCATTGATGGC
176   S  V  T  R  P  L  D  R  E  A  I  A  N  Y  E  L  E  V  E  V  T  D  L  S  G  K  I  I  D  G

721  CCAGTCCGCCTAGATATTTCTGTTATTGATCAAAATGATAACAGGCCGATGTTCAAAGAAGGACCCTATGTTGGTCACGTCATGGAAGGA
206   P  V  R  L  D  I  S  V  I  D  Q  N  D  N  R  P  M  F  K  E  G  P  Y  V  G  H  V  M  E  G

811  TCCCCTACAGGAACAACTGTGATGCGGATGACAGCATTTGATGCTGATGATCCTAGCACAGACAACGCTCTCTCGGTATAACATCTC
236   S  P  T  G  T  T  V  M  R  M  T  A  F  D  A  D  D  P  S  T  D  N  A  L  L  R  Y  N  I  L

901  AAGCAGACACCTACCAAACCTTCCCACAAATATGTTCTACATTGACCCTGAGAAAGGAGATATTGTCACAGTGGTCGCCTGTACTGTG
266   K  Q  T  P  T  K  P  S  P  N  M  F  Y  I  D  P  E  K  G  D  I  V  T  V  V  S  P  V  L  L

991  GATCGTGAGACAATGGAAACCGCCAAGTACGAGCTGGTTATTGAAGCCAAGGATATGGGCGGCCATGATGTGGGACTTACTGGAACTGCA
296   D  R  E  T  M  E  T  P  K  Y  E  L  V  I  E  A  K  D  M  G  G  H  D  V  G  L  T  G  T  A
```

FIG.2D

```
1081  ACTGCCACTATTCTTATTGATGACAAAAACGACCACCCAGAATTACCAAGAAGGAGTTTCAGGCCACAGTAAAGGAAGGAGTCACA
 326   T  A  T  I  L  I  D  D  K  N  D  H  P  P  E  F  T  K  K  E  F  Q  A  T  V  K  E  G  V  T

1171  GGAGTAATAGTAAACTTAACTGTTGGTGACCGAGATGACCCAGCAACTGGAGAGCATGGAGAGCTGTCTACACTATTATTAACGAAATCCA
 356   G  V  I  V  N  L  T  V  G  D  R  D  D  P  A  T  G  A  W  R  A  V  Y  T  I  I  N  G  N  P

1261  GGGCAGAGTTTTGAAATCCATACCAATCCCCAGACTAATGAGGGAATGCTCTCTGTTGTCAAACCTTTAGACTATGAGATTTCAGCATTT
 386   G  Q  S  F  E  I  H  T  N  P  Q  T  N  E  G  M  L  S  V  V  K  P  L  D  Y  E  I  S  A  F

1351  CACACATTGCTGATAAAAGTAGAAAATGAAGACCCCGTTGATTCCAGATCCACAGCAACAGTTCAGATCACC
 416   H  T  L  L  I  K  V  E  N  E  D  P  L  I  P  D  I  A  Y  G  P  S  S  T  A  T  V  Q  I  T

1441  GTTGAGGATGTGAATGAAGGCCCTGTTTTCCACCCAAACCCAATGACAGTGACAAAACAAGAGAACATCCCTATTGGCAGCATTGTGTTA
 446   V  E  D  V  N  E  G  P  V  F  H  P  N  P  M  T  V  T  K  Q  E  N  I  P  I  G  S  I  V  L

1531  ACAGTAAATGCCACTGATCCAGATACTTTGCAACATCAGAGGATCCAGTTTACAGGTATTCAGTTCGAACATCAGAGATTAAT
 476   T  V  N  A  T  D  P  D  T  L  Q  H  Q  T  I  R  Y  S  V  Y  K  D  P  A  S  W  L  E  I  N

1621  CCCACCAATGGTACCGTTGCCACCACTGCTGTCTGTGTTAGGATAACAAATACTGCTCTCCTGGCA
 506   P  T  N  G  T  V  A  T  T  A  V  L  D  R  E  S  P  H  V  Q  D  N  K  Y  T  A  L  F  L  A

1711  ATAGACAGTGGTAACCCTCCTGCTACAGGTACAGGAACTTTACACATCACCTTGGAGGACGTCAATGACAATGTCCCCTTTACCA
 536   I  D  S  G  N  P  P  A  T  G  T  G  T  L  H  I  T  L  E  D  V  N  D  N  V  P  S  L  Y  P

1801  ACACTGGCAAAAGTCTGTGATGATGCTAAAGATCTCAGAGTGGTTCTAGGAGCATCAGACAAAGACCTCCATCCAACACAGATCCA
 566   T  L  A  K  V  C  D  D  A  K  D  L  R  V  V  L  G  A  S  D  K  D  L  H  P  N  T  D  P
```

FIG.2E

```
1891  TTTAAATTGAACTGAGTAAGCAATCTGGTCCAGAAAAGTTATGGAGAATCAACAAGCTTAACAATACTCATGCCCAGGTTGTCCTGCTT
596    F  K  F  E  L  S  K  Q  S  G  P  E  K  L  W  R  I  N  K  L  N  N  T  H  A  Q  V  V  L  L

1981  CAAAACCTGAAAAGCCAATTACACACATCCCAATTCCCAGTGACAGATTCTGAAACCACCTCTGACTAACACAGAACTGAAATTA
626    Q  N  L  K  K  A  N  Y  N  I  P  I  S  V  T  D  S  G  K  P  P  L  T  N  T  E  L  K  L

2071  CAAGTGTGTCCTGCAAGAAATCCAGAATGGACTGCAGTGCAAGTGCAAGTGATCCCTTCATATCAGCATGACTCTTATCCTCTTCACTCTTC
656    Q  V  C  S  C  K  K  S  R  M  D  C  S  A  S  D  A  L  H  I  S  M  T  L  I  L  S  L  F

2161  AGTTTATTTGTAAGTCTTTCCTTATGTGTAAGCATTGAACGTTATTTATCTCGTTTGCACTATAAGAAACTTACCAAGAGAG
686    S  L  F  C  K  S  F  P  Y  V  *

2251  AAGTTAACTTATTTTCCCTGCGGTAGATGCTATACAGAAGTAGGAGGGGAGGATTTTCACAGTCAAAAAATAGCAACAAATGCCG
2341  GGTTGTCAAATTAAGAAATAGAAGCAATAATTCTAGGAAGAATCAAAGAATTAAACTAGCATATGATAAACTAAGAAGTACCAGCTG
2431  TAGTAACAGATTTCTGAGATGCTTTCTTCATCTCTCCCACTGTCTCTCAATTCAATTCATTTGTCCGTAAAGTGCCGAGCAATTGGAACATAAGG
2521  AACAATAACTGTCTGGGTCACCATGGAAAATGAGTACTGTCTCCTCTTCAATCTATTTGTCCGTAAAGTGCCGAGCAATTGGAACATAAGG
2611  AACTTACTGAAGATTCTGGGTTTAGAGAAGCTTTCTAAAAGTCTTATGAAAGTCTTATGAATTCCTAAAACCAGTCTGAATTAGGAGTTTAAAGG
2701  GAAGCTTCTGCTTGCTTTAGAGAAAGCTTTCTAAAAGTCTTATGAAATTCCTAATCTGAATTAGGAGTTTAAAGGAATTC
```

FIG.2F

```
SIG T  MQHKTQLTLSFLLSQVL..LLACA.....
    N  MCRIAGTPPRILPPLALMLLAALQQAPI
    L  ...........................
    E  MGARCRSFSALLLLLQVSSWLCQELEP.
    P  MELLSGPHAFLLLLLQVCWLRSVVSEP.

PRE T  ....EDLECTPGFQQKV.FYIEQPFEFTE.DQPILNLVFDDCKGNNKLNFEVSNP.DFKVEHDGSLVA.L
    N  KATCEDMLCKMGFPEDV.HSAVVSRSVHG.GQPLLNVRFQSCDENRKIYFGSSEPEDFRVGEDGVVYAER
    L  ......................DSVAA.GRELGRVSFAACS.GRPWAVYVPTDTRFKVNGDGVVSTKR
    E  ......ESCSPGFSSEV.YTFPVPERHLERGHVLGRVRFEGCT.GRPRTAFFSEDSRFKVATDGTITVKR
    P  ........YRAGFIGEAGVTLEVEGTDLEPSQVLGKVALAGQG..................

EC1 T  AILATPILIPENQR.PPFPRSVGKVIRSEGTEGA.....KFRLS..GKGVDQDPKGIFRINEIS.....G
    N  DWVIPPINLPENSR.GPFPQELVR.IRSDRDKSL.....SLRYSVTGPGADQPPTGIFIINPIS.....G
    L  DWVIPPISCLENHR.GPYPMRLVQ.IKSNKDKES.....KVYYSITGQGADSPPVGIFIIERET.....G
    E  DWVIPPISCPENEK.GEFPKNLVQ.IKSNRDKET.....KVFYSITGQGADKPPVGVFIIERET.....G
    P  EWVMPPIFVPENGK.GPFPQRLNQ.LKSNKDRGT.....KIFYSITGPGADSPPEGVFTIEKES.....G
       **  **     *           *          * * * ** *            *

EC2 T  KEGPYVGHVMEGSPTGTTVM...RMTAFDADD.PSTDNALLRYNILKQTPTKPSPNMFYIDPEK.....G
    N  LHQVWNGTVPEGSKPGTYVM...TVTAIDADD.PNAQNGMLRYRILSQAPSSPSPNMFTINNET.....G
    L  IKEVFVGYIEENAKPGTSVM...TVNATDADDAVNTDNGIVSYSIVSQQPPRPHPQMFTIDPAK.....G
    E  TQEVFEGSVAEGAVPGTSVM...KVSATDADDDVNTYNAAIAYTIVSQDPELPHKNMFTVNRDT.....G
    P  TQDTFRGSVIEGVMPGTSVM...QVTATDEDDAVNTYNGVVAYSIHSQEPKEPHDLMFTIHKST.....G
       *       *   ** **        * **        *      *   * * *    **        *

EC3 T  TKKEFQATVKEG.VTGVIV.NL.TVG..DRDD.PATGAWRAVYTIINGN...P.GQSFEIHTNPQTNE.G
    N  TAMTFYGEVPEN.RVDVIVANL.TVT..DKDQ.PHTPAWNARYQMTGD...PTGQ.FTILTDPNSND.G
    L  NPSTYQGQVPEN.KPGTEVARL.TVT..DQDA.PGSPAWQAVYHIKSGN..LDGA.FSIITDPSTNN.G
    E  NPSTYQGVPEN.EVNARIATL.KVT..DDDA.PNTPAWKVVYTVV.ND...PDQQ.FVVVTDPTTND.G
    P  EPQKYEAWVPEN.EVGHEVQRL.TVT..DLDV.PNWPAWRATYHLVGGD...DGDH.FTITTHPETNQ.G
       * *                 * *    * * *  *   * **  *              *  * * *

EC4 T  HPNPMTVTKQENIPIGSIVL...TVNATDPDTLQHQT...IRYSVYKD....PASWLEI...NPTN...G
    N  VPNPKLVRQEEGLLAGSMLT...TFTARDPDRYMQQT..SLRYSKLSD...PANWLKI...DPVN...G
    L  VPPIKRVGVPEDLPVGQQVT...SYTAEDPDRDMRQ...KITYRMGSD...PAGWLYI...HPEN...G
    E  MPAERRVEVPEDFGVGQEIT...SYTAREPDTFMDQ...KITYRIWRD...TANWLYI...NPET...G
    P  VPPSKVIEAQEGISTGELVC...IYTAQDPDKE.DQ...KISYTISRD...PANWLAV...DPDS...G
       *      *   *   *      * **   *         * *    *    ** **   *

EC5 T  SLYPTLAKVCDDAKDLRVV....VLGASDKDLHPNTDPFKFELSKQSGPE..KL.W..RINKLN..NTHA
    N  QVNPKEATTCETLQPNAIN.....ITAVDPDIDPNAGPFAFELPD.SPPSI.KRNW..TIVRIS..GDHA
    L  TPEPRSFEICSR.QPEKQI.....LSIVDKDLPPHTYPFKAALEH.GSS...NNW..TVEIRG..QDEL
    E  IPEPRNMQFCQR.NPQPHI.....ITILDPDLPPNTSPFTAELTH.GAS...VNW..TIEYNDAAQESL
    P  IPEPRQIIICNQ.SPVPQV.....LNITDKDLSPNSSPFQAQLTH.DS.DI...YW..MAEVSE.KGDTV
       *      *               * ** *  *   *      *          *

TM  T  .......ALHISMTLILLSLFSLFCL*
    N  ..IVGAGLGTGAIIAILLCIIILLILVLMFVVWM
    L  ..IVG.GLGVPAILGILGGILALLILLLLLLFA
    E  AGIVAAGLQVPAILGILGGILALLILILLLLLFL
    P  ....G.GFILP.ILGAV...LALLTLLLALLLLV
                           *  *

CP  T
    N  KRRDKERQAKQLLIDPEDDVRDNILKYDEEGGGEEDQDYDLSQLQ.QPDTVEPDAIKPVGIRRLDERP.IHAEPQYPVRSAAP
    L  RRRKVEKEP..LLP.PEDDMRDNVYNYDEEGGGEEDQDYDLSQLHRGLDAR.PEVI......RNDVAPPLMAAPQYRPRPA..
    E  RRRTVVKEP..LLP.PDDDTRDNVYYYDEEGGGEEDQDFDLSQLHRGLDAR.PEVT......RNDVAPTLMSVPQYRPRPA..
    P  RKKRKVKEP..LLL.PEDDTRDNVFYYGEEGGGEEDQDYDITQLHRGLEAR.PEVVL.....RNDVVPTFIPTPMYRPRPA..

T
    N  HPGDIGDFINEGLKAADNDPTAPPYDSLLVFDYEGSGSTAGSLSSLNSSSSGGEQDYDYLNDWGPRFKKLADMYGGG..DD*
    L  NPDEIGNFIDENLKAADTDPTAPPYDSLLVFDYEGGGSEATSLSSLNSSASDQDQDYDYLNEWGNRFKKLAELYGGGEDDE*
    E  NPDEIGNFIDENLKAADSDPTAPPYDSLLVFDYEGSGSEAASLSSLNSSESDQDQDYDYLNEWGNRFKKLADMYGGGEDD*
    P  NPDEIGNFIIENLKAANTDPTAPPYDSLMVFDYEGSGSDAASLSSLTTSASDQDQDYNYLNEWGSRFKKLADMYGGGEDD*
```

FIG. 3A

```
KNVSEAGRALF..VHAR..SEHAE...DMAEILI.VGADEKHDALKEIFKIEGNLGIP.........RQKR
SFQLSAEPTEFVVSARDKETQEEWQMKVKLT.PEPAFTGASEKDQKKIEDIIFPWQQYKDSSHLKRQKR
PLTLYGRKISFTIYAQDAMGKR.HSARVTV..GRHRHRRHHHNHHLQDTTPAVLTFPKHDPGFLRRQKR
HLKLHKLETSFLVRARDSSHRE..LSTKVTLKSMGHHHHRHHHRDPASESNPELLMFPSVYPG.LRRQKR
..........................MHHADNGDIIMLTRGTVQGGKDAMHSPPTRILRRRKR
                                                              *  **

DVSVTRP...LDRE.....AIANYELEVEVTDLSGKIIDG.........PVRLDISVIDQNDNRPMF
QLSVTKP...LDRE.....QIASFHLRAHAVDVNGNQVEN.........PIDIVINVIDMNDNRPEF
WLEVTEQ...LDRE.....KIDRYTLLSHAVSASGQPVED.........PMEIITTVMDQNDNKPVF
WLKVTQP...LDRE.....AIAKYILYSHAVSSNGEAVED.........PMEIVITVTDQNDNRPEF
WLLLHMP...LDRE.....KIVKYELYGHAVSENGASVEE.........PMNISILVTDQNDNKPKF
          ****     *   *        *               *   *   * **  * *

DIVTVVSPVLLDRE...TMETPKYELVIEAKDMGGHDV..GLTG.....TATATILIDDKNDHPPEF
DIITVAAG..LDRE.....KVQQYTLIIQATDMEGNPTY.GLSN.....TATAVITVTDVNDNPPEF
IISVLGTG..LDRE.....TTPNYTLIVQATDQEGK....GLSN.....TATALIEVTDANDNIPIF
VISVLTSG..LDRE.....SYPTYTLVVQAADLQGE....GLST.....TAKAVITVKDINDNAPVF
TISVISSG..LDRE.....KVPEYRLTVQATDMDGE....GSTT.....TAEAVVQILDANDNAPEF
*         ****     *  *  * *    *               ** *   * **  * *

.MLSVVKP..LDYE.....ISAFHTLLI.KVE..NEDPLIPDIAYGPSS.TATVQITVEDVNE.GPVF
.LVTVVKP..IDFE.....TNRMFVLTV.AAE..NQVPLAKGIQHPPQS.TATVSITVIDVNE.SPYF
ILKTA.KG..LDYE.....TKSRYDLVV.TVE..NKVPLS.VPITLS...TASVLVTVLDVNE.PPVF
ILKTA.KG..LDFE.....AKQQYILHV.RVE..NEEPFE.GSLVPS...TATVTVDVVDVNE.APIF
VLTTK.KG..LDFE.....AQDQHTLYV.EVT..NEAPFA.VKLPTA...TATVVVHVKDVNE.APVF
     * *              *         *  *             ** *   * ****  * *

TVATTAV...LDRESP.HVQDNKYTALFLAID.SGNPPATG........TGTLHITLEDVNDNVP
QITTTAV...LDRESI.YVQNNMYNATFLASD.NGIPPMSG........TGTLQIYLLDINDNAP
.IVTATQP..LDRESV.HAINSTYKAIILAVD.NGIPDTTG........TGTLLLLLQDVNDNGP
AIFTRAE...MDREDAEHVKNSTYVALIIATD.DGSPIATG........TGTLLLVLLDVNDNAP
QI.TAAGI..LDREDEQFVKNNVYEVMVLATD.SGNPPTTG........TGTLLLTLTDINDHGP
*         ***    *    *  *  *                   ****   * **  *

QVVL..LQNLKKAN........YNIPISVTD.SGKPPLTNNTELKLQVCSCK.KSRMDCSASD.
QLSL..RIRFLEAGI.......YDVPIVITD.SGNPHASSTSVLKVKVCQCD.ING.DCTDVDR
AMGL...KKELEPGE.......YNIFVKLTD.SQGK.AQVTQV.KAQVCECEGTAKN.CERRSY
ILQP...RKDLEIGE.......YKIHLKLAD.NQNKD.QVT.TLDVHVCDCEGTVNN.CMK...
ALSL...KKFLKQDT.......YDLHLSLSD.HGNRE.QLT.MIRATVCDCHGQVFNDCPRPWK
       *              *       *                 ** *        *
```

FIG. 3B

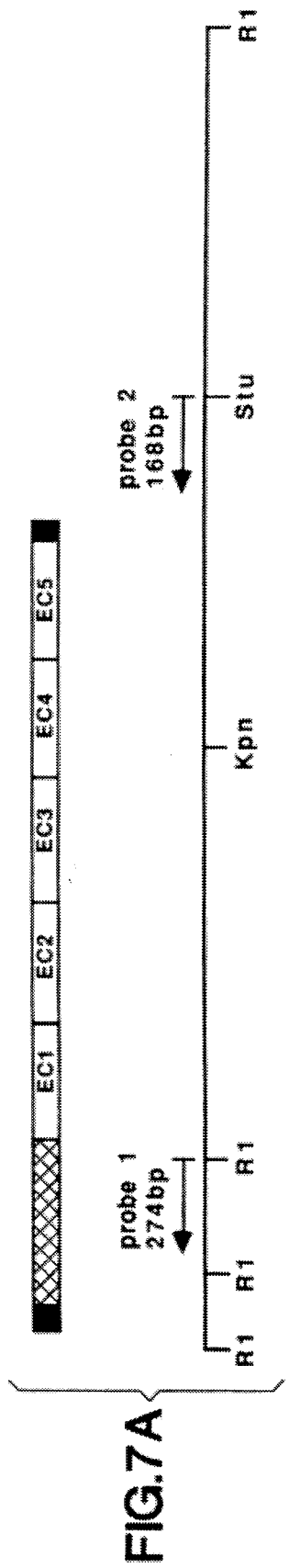
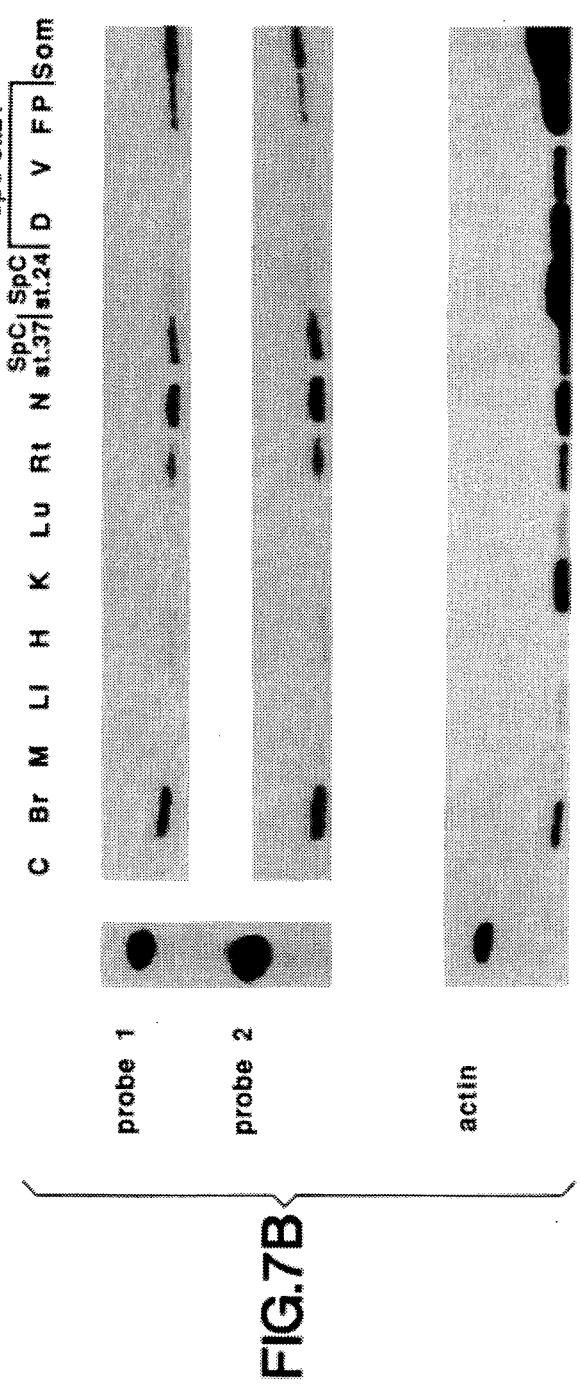
FIG.7A
FIG.7B

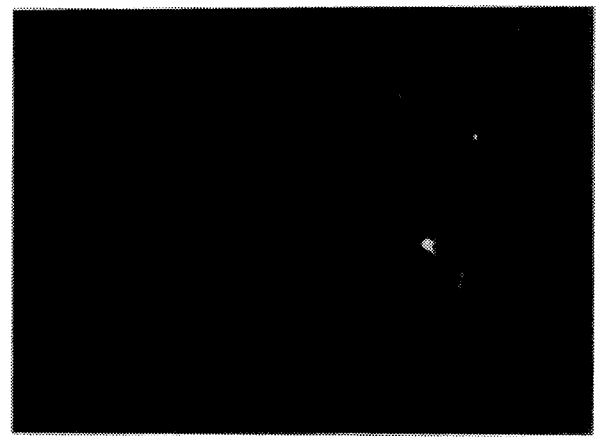
FIG.8F
FIG.8E
FIG.8D

T-CADHERIN ADHESION MOLECULE

This invention was made with government support under grant number P01 HD 25938 awarded by the National Institutes of Health. The government has certain rights in the invention.

This application is a continuation of application Ser. No. 07/607,293 filed Oct. 30, 1990, now abandoned.

BACKGROUND OF THE INVENTION

This invention relates to cell surface molecules and more specifically to T-cadherin, a new cell adhesion molecule of the cadherin family.

Cadherins are a family of transmembrane glycoproteins that mediate adhesive interactions in the developing and adult organism through a Ca2+-dependent mechanism (Takeichi, 1988 and 1990, review). It has been suggested that the cadherins arose from a common ancestral gene. Duplication of the gene may have resulted in the formation of a structurally related family of molecules with heterogeneous sequences. Cadherins share their overall structure which, at the extracellular region, is subdivided into a signal peptide, a prepeptide and five related extracellular domains and is followed by a transmembrane domain and a highly conserved stretch of cytoplasmic amino acids, that is suggested to provide a linkage with the cell's cytoskeletal network. The signal peptide and the prepeptide are readily cleaved and are absent from the mature protein. Several members of the cadherin family have been characterized. N-cadherin is found in the nervous system during development and has been shown to be a strong mediator of nerve fiber growth in vitro. In addition to neural tissue, N-cadherin is also expressed in heart and skeletal muscle and in lens cells. E-cadherin (also known as uvomorulin in the mouse) is a component of epithelial cells and P-cadherin is found in placenta.

T-cadherin, which is subject of this application, is a novel member to the cadherin family that shares the overall cadherin structure in the extracellular region, but lacks the conserved cytoplasmic sequences. Therefore, a new mode of T-cadherin function is proposed, in which T-cadherin regulates the adhesive cell properties not through a direct linkage with the cytoskeleton, but through higher membrane mobility and ready access to its extracellular ligand. The pattern of T-cadherin expression suggests a key role in the establishment of the pattern of nerve fiber growth in developing embryos. Furthermore, T-cadherin is the first molecularly characterized polypeptide to be identified in a segmental pattern as epithelial somites undergo the transition to form the dermamyotome and sclerotome. The expression in only one half of the somitic sclerotome, that eventually will give rise to vertebrae, suggests that T-cadherin plays a key role in the segmentation of vertebrate embryos. Segmentation is a crucial property of the vertebral column that allows flexibility and provides an individual with the ability to bend the back. T-cadherin has also been identified in muscle cells and blood vessels. In muscle, T-cadherin may be involved in cell differentiation and function. Expression in blood vessels may suggest that T-cadherin may be associated with the vascularization of tumors. A tumor remains small unless provided with blood capillaries. The control of vascularization that may be possible with the reagents described in this invention, may therefore be useful in controlling tumor formation and metastasis.

The identification of molecules which regulate and direct nerve fiber growth is important to the study of nerve regeneration. After being severed, neurons either degenerate or remain in a state of severe atrophy. The prognosis for recovery of these damaged neurons is very poor. Therefore, the use of molecules such as the T-cadherin cell adhesion molecules may influence neurons to regrow their axons and guide the axons to reinnervate their corresponding target cells. Eventually, this may lead to relief from the disabling effects of stroke or trauma to the nervous system.

There thus exists a need for the identification and characterization of cell surface adhesion molecules which may be involved in regulation of development in the embryo or recovery of traumatized neurons including methods of detecting and utilizing these molecules. The present invention satisfies this need and provides related advantages as well.

SUMMARY OF THE INVENTION

The invention provides substantially purified T-cadherin polypeptides and isolated nucleic acids which encode the T-cadherin polypeptides. Antibodies reactive with various forms of T-cadherin, but not reactive with N-, E- or P-cadherin are also provided. The invention provides methods for detecting the various forms of T-cadherin in a subject as well as a method of detecting tumor growth which consists of inhibiting the activity of T-cadherin in a tumor. A method of effecting traumatized neurons is provided. The method entails treating traumatized neurons with a therapeutically effective dose of T-cadherin.

BRIEF DESCRIPTION OF THE DRAWINGS

Figure 2C:
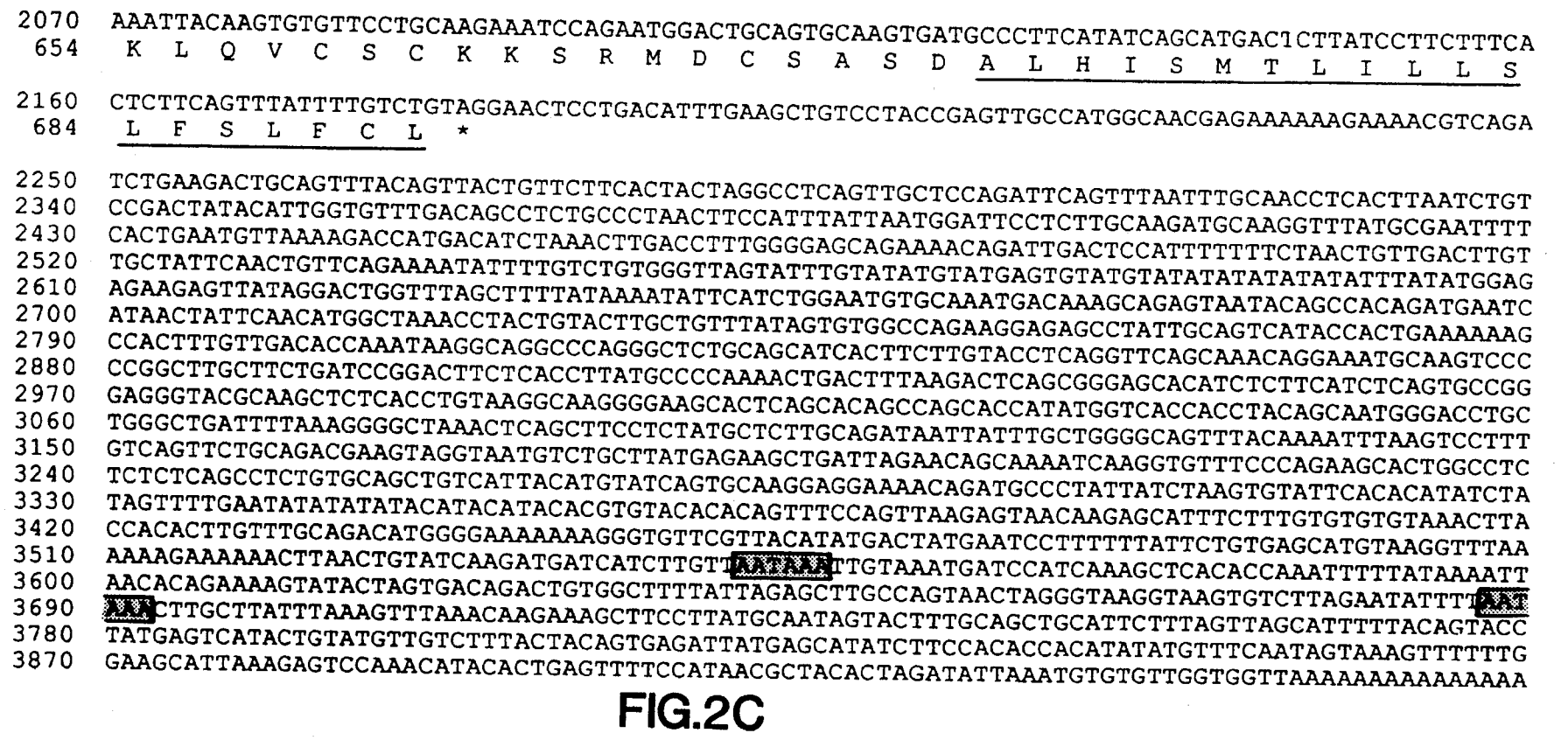

FIG. 2 shows the nucleotide and predicted amino acid sequence of the T-cadherins. FIGS. 2a, b, c the sequences of T-cadherin 1. FIG. 2d, e, f shows the sequences for T-cadherin 2.

FIGS. 3a, b shows the amino acid alignment of T-cadherin 1 (266 cDNA) with the related proteins N-cadherin, L-CAM, E-cadherin and P-cadherin.

FIGS. 7a, b shows a RNase protection assay of T-cadherin mRNA. Samples are BR=brain, M=muscle, LI=liver, H=heart, K=kidney, LU=lung, RT=retina from hatched chickens. N=cultured sympathetic neurons as in Example 5. Spinal cord H/H stage 37 and 24. Spinal cord H/H stage 24 separated into D=dorsal, V=ventral and FP=floor plate region. SOM=somites.

DETAILED DESCRIPTION OF THE INVENTION

Figure 1:
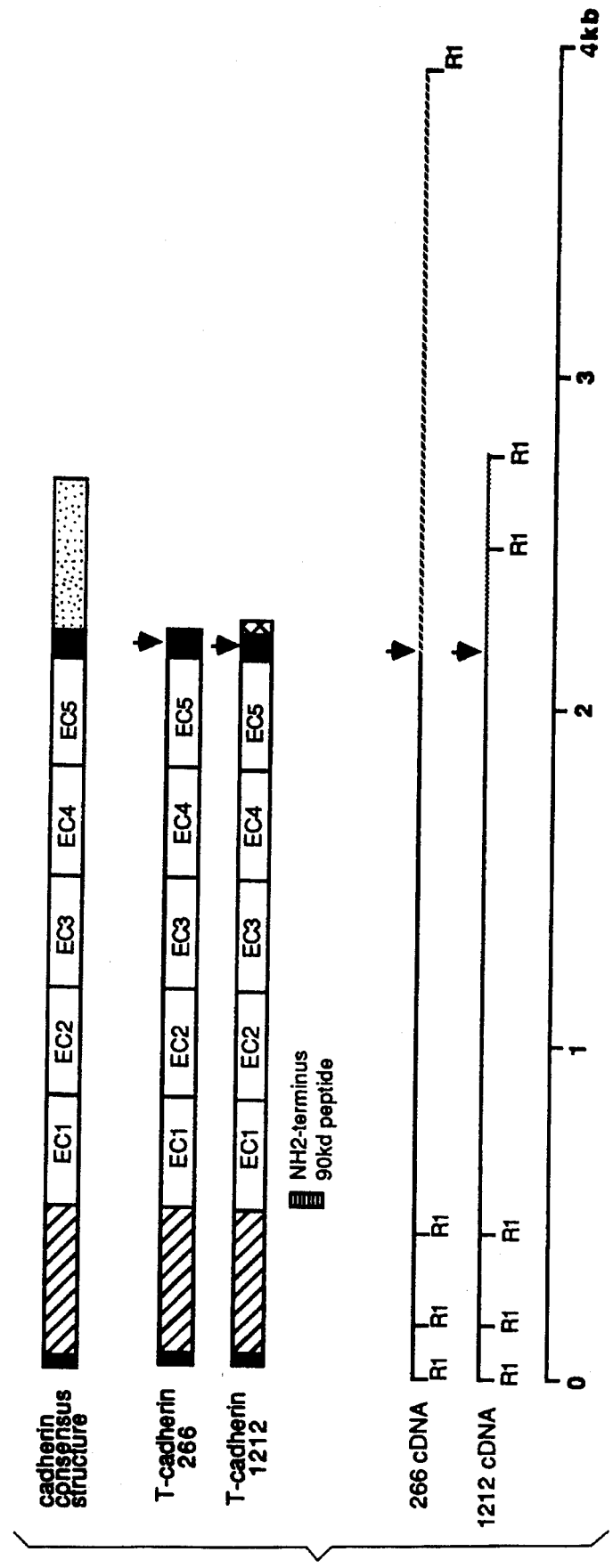
FIG. 1 shows the STRUCTURAL alignment of T-cadherin 1 (266 cDNA) and T-cadherin 2 (1212 cDNA) with the cadherin consensus structure.

T-cadherin ("T-cad;"T=truncated) is a member of the cadherin family of cell adhesion molecules. T-cadherin may be involved in the development of the embryo or recovery of traumatized neurons and therefore may be useful in nerve regeneration. T-cadherin is expressed in the nervous system, as well as the heart, skeletal muscle, blood vessels and the muscle lining the gut and skin. The high expression of T-cadherin in blood vessels may be important in the development of highly vascularized tumors.

T-cadherin shares some but not all structural features of other cadherins. The structural similarity extends to the amino acid level in that the extracellular portion of T-cadherin shows 35–47% identity with the extracellular domains of N-cadherin, E-cadherin, P-cadherin and L-CAM; N-cadherin with 47% amino acid identity being most closely related. Two forms of T-cadherin identified in the present invention lack the cytoplasmic portion found in all other members of the cadherin family. One form of T-cadherin, herein referred to as T-cad 1, appears to be anchored to the membrane through a glycosyl phosphatidylinositol (GPI) linkage. Biochemical evidence for such a linkage has been obtained by showing that T-cadherin can be released from the cellular plasma membrane by phosphatidylinositol specific phospholipase C and can incorporate radiolabeled ethanolamine into the GPI linkage. The other form of T-cadherin, T-cad 2, is predicted by the cDNA to contain sequences for a hydrophobic domain followed by 5 cytoplasmic amino acids. From preliminary transfection of this cDNA into COS-cells, it is likely that this form is also GPI-linked. These data provide evidence for a membrane linkage of T-cadherins that differs from known cadherins, in particular, in their proposed association with the cytoskeleton. In summary, T-cadherin is a member of the cadherin family of cell adhesion molecules that differs in its anchorage to the plasma membrane from known cadherins.

cDNAs have been isolated that encode T-cad 1 and T-cad 2, two closely related, but distinct forms of T-cadherin (FIGS. 2a, b, c and 2d, e, f). The extracellular portion of both forms are identical and contain structural features characteristic of the cadherin family. The two forms differ in their COOH-terminal region in that T-cad 2 cDNA encodes five additional amino acids (FIGS. 3a, b). The absence of a cytoplasmic domain can allow for greater mobility of these molecules within the cell membrane and therefore modulate adhesive cell properties.

RNA transcripts encoding both forms of T-cadherin have been detected using RNAse protection probes specific for each form. There is evidence that the different forms of T-cadherin may be developmentally regulated both temporally and in a tissue specific fashion.

As used herein, "T-cadherin" or "T-cad" refers to polypeptides having substantially the amino acid sequence in FIGS. 2a, b, c and 2d, e, f, and which are cross-reactive with antibodies reactive with T-cad, but not with N-cadherin, E-cadherin, P-cadherin and L-CAM. Polypeptides comprising the extracellular, transmembrane and truncated cytoplasmic domain of T-cad 1 and T-cad 2 are provided. Minor modifications of the sequence which do not destroy its immunoreactivity also fall within the definition of the protein claimed.

The suggested open reading frame of T-cadherin cDNAs, T-cad 1 and T-cad 2, encode 690 and 695 amino acid proteins, respectively, of predicted molecular mass 76,018 and 76,627 daltons.

It is understood that limited modifications may be made without destroying the biological function of T-cadherin, and that only a portion of the entire primary structure may be required to effect activity. Minor modifications of the primary amino acid sequence may result in proteins which have substantially equivalent or enhanced function.

As used herein, "T-cadherin" refers to a cell adhesion polypeptide having an amino acid sequence substantially equivalent to that shown in FIGS. 2a, b, c and 2d, e, f and may be involved in the development of the embryonal nervous system and in recovery of traumitized neurons.

"Substantially purified," when used to describe the state of T-cadherin, denotes the protein substantially free of the other proteins and molecules normally associated with or occurring with T-cadherin in its native environment.

"Nucleic acid encoding" as used herein, refers to the primary nucleotide sequence of a gene which provides the order of corresponding amino acids in the protein that they specify. Examples of the cadherin nucleic acid sequence are presented in FIGS. 2a, b, c and 2d, e, f.

The invention provides nucleic acids (DNA, RNA, or cDNA) encoding the polypeptides of the invention. The nucleic acid may or may not be expressed in the native host. Vectors comprising these nucleic acids are also provided. Numerous cloning vectors are known to those of skill in the art, and the selection of an appropriate cloning vector is a matter of choice. "Transformed host cells" refers to cells which have had vectors, constructed using recombinant DNA techniques, introduced to them. Host cells can be transformed with such a vector and used to express recombinant polypeptides. Host cells can be mammalian, yeast, insect, or bacterial as long as the appropriate vector is used. Methods of recombinant expression are well known in the art, see Maniatis et al., MOLECULAR CLONING: A LABORATORY MANUAL (1982), which is incorporated herein by reference. Thus, recombinant polypeptides and the method of their production are also provided.

The vectors and methods disclosed herein are suitable for use in host cells including a wide range of prokaryotic and eukaryotic organisms. It is understood that "cells" or "host cells" refers not only to the particular subject cell, but also to the progeny of such a cell. The invention provides vectors which are capable of expressing DNA sequences contained therein, where such sequences are operably linked to other sequences capable of effecting their expression. It is implied that these expression vectors must be replicable in the host organism either as episomes or as an integral part of the chromosomal DNA.

Additionally, recombinant DNA methods currently used by those skilled in the art include the polymerase chain reaction (PCR), which, combined with the synthesis of oligonucleotides, allows easy reproduction of DNA sequences. A DNA segment can be amplified exponentially starting from as little as a single gene copy by means of PCR. In this procedure, a denatured DNA sample is incubated with two oligonucleotide primers that direct the DNA polymerase-dependent synthesis of new complementary strands. Multiple cycles of synthesis each results in an approximate doubling of the amount of target sequence. After twenty-five amplification cycles, the amount of target sequence increases by approximately $10^6$-fold. Amplification of first strand cDNAs using the polymerase chain reaction has been used to detect both forms of T-cadherin. The PCR technology is the subject matter of U.S. Pat. Nos. 4,683,195; 4,800,159; 4,754,065 and 4,683,202, all of which are incorporated by reference herein. The cDNAs shown in FIGS. 2a, b, c and 2d, e, f, or any portion of the sequence can be reproduced for cloning and expression purposes by amplifying the desired sequence with PCR and cloning it into a suitable vector, as is well known in the art.

Detection methods for the presence of nucleic acid or protein in cells include hybridization of a nucleic acid probe with the nucleic acid of a cell and cell staining with polyclonal or monoclonal antibodies. Such techniques are accomplished by methods well-known to those skilled in the art.

Polyclonal antibodies against T-cadherin were prepared according to procedures well known in the art. The specificity of the antibodies was examined by carrying out immunohistochemistry and immunoblotting of various tissues including neuronal cells and somites.

Alternatively, anti-T-cadherin antibodies can be prepared by immunizing an animal with synthetic peptides or recombinant protein fragments prepared from the sequence shown in FIGS. 2a, b, c and 2d, e, f as is well known in the art. Selection of anti-T-cadherin antibodies is performed as described above.

Monoclonal antibodies are prepared by immunizing an animal with material containing T-cadherin or synthetic peptides or recombinant protein fragments thereof, followed by isolating antibody-producing hybridoma cells, as is well known in the art. (See, for example, Harlow and Lane, ANTIBODIES: A LABORATORY MANUAL, Cold Spring Harbor, 1988, and the references cited therein, all which are incorporated herein by reference.) Anti-T-cadherin antibodies are selected by performing immunofluorescence analysis of tissue sections where T-cadherin is localized. The identification of antibodies is confirmed by immunoblotting and immunoprecipitation which reveals the predominant 90 kD polypeptide described above. The appropriate hybridoma is reactive with purified T-cadherin or T-cadherin fragments. T-cadherin fragments can be prepared by expressing the T-cadherin cDNAs shown in FIGS. 2a, b, c and 2d, e, f in a prokaryotic or eukaryotic expression vector as described above.

Methods of detecting T-cadherin in a subject are also provided. T-cadherin can be detected in a cell sample by using immunological techniques such as labeled antibodies. Such methods including the choice of label are known to those ordinarily skilled in the art. (Harlow and Lane, Supra). Briefly a subject's tissue sample is exposed first to an antibody specific for T-cadherin. After binding of the antibody, a second antibody, appropriately labeled and specific for the anti-T-cadherin antibody, is exposed to the sample previously incubated with the T-cadherin antibody. The secondary antibody can then be visualized or quantitated and the presence of T- cadherin detected. The invention provides a method of inhibiting tumor growth by inhibiting vascularization of the tumor. Treatment of the tumor with anti-T-cadherin antibodies reduces T-cadherin expression and the amount of vascularization.

The invention also provides a method of repairing traumatized neurons of a subject, including trauma due to stroke or injury. Administration of T-cadherin in the region of the traumatized neurons may influence neurons to regrow their axons and guide the axons to reinnervate their target cells.

The following examples are intended to illustrate but not limit the invention. While they are typical of those that might be used, other procedures known to those skilled in the art may alternatively be employed.

EXAMPLE I

Isolation of T-Cadherin

T-cadherin was identified as a concanavalin A-binding glycoprotein in the detergent-resistant membrane skeleton of chicken sympathetic neurons and embryo brain. The membrane skeleton was isolated as a non-ionic detergent resistant polypeptide complex was isolated in buffer A (10 mM Tris/HCl, pH 7.6, 2 mM $CaCl_2$, 5% Nonident P40, 2 mM dithiothreitol, 1 mM phenylmethylsulfonyl fluoride, 50 µM leupeptin, 5 µM pepstatin, 4 ng/ml aprotinin) from 13–16 day old chick embryo brains. The 90 kD fragment of T-cadherin was separated from the complex by preparative SDS gel electrophoresis (Laemmli, Nature 227:680–685 (1970)) as described above. Next to contactin, a 130 kD cell adhesion molecule of the immunoglobulin supergene family, T-cadherin is the major concanavalin A-binding glycoprotein of the complex (Ranscht et al., J. Cell Biol. 99:1803–18113 (1984)). The migration of T-cadherin on SDS-PAGE gels under reducing and non-reducing conditions is closely similar, suggesting that few or no intrachain disulfide bonds are present. Protein complexes containing T-cadherin, contactin, actin and approximately 15 other polypeptides were enriched by differential centrifugation and ion-exchange chromatography. The isolated protein complexes resist extraction with a variety of detergents in different salt conditions; thus, the individual components can only be dissociated from the complexes under denaturing conditions. T-cadherin can be purified by SDS preparative gel electrophoresis with a yield of approximately 50 µg from 50 g starting material.

EXAMPLE II

Protein Microsequencing

Proteins contained in brain polypeptide complex (BPC) were separated by preparative SDS-PAGE and electrophoretically transferred to a polyvinylidene difluoride membrane (Millipore, Burlington, Mass.) by methods well known to those skilled in the art. The 90 kD T-cadherin polypeptide was identified by staining the transferred proteins with Coomassie Brilliant Blue R250, excised and sequenced directly. Transfer conditions and processing were as described by Matsudaira, P., J. Biol. Chem. 262:10035–10038 (1987).

EXAMPLE III

Generation and Affinity Purification of Anti-T-Cadherin Antiserum

The detergent-resistant polypeptide complex was separated into its individual components by preparative SDS-PAGE gel electrophoresis. The 90 kD T-cadherin fragment was excised from several Coomassie-blue stained gels, electroeluted and desalted on exocellulose GF5 (Pierce, Rockford, Ill.). A New Zealand white rabbit was immunized by intramuscular and subcutaneous injections of 100 µg 90 kD T-cadherin polypeptide in Freund's complete adjuvant (1:1). The rabbit was boosted three times in four week intervals with an identical amount of protein in Freund's incomplete adjuvant. Final boosts were intravenous with 50–100 µg protein in phosphate-buffered saline (PBS). Blood was collected 7–10 days after the injections. The antiserum was absorbed on bovine liver acetone powder.

For some experiments, affinity purified antiserum was used. Affinity purification was achieved with T-cadherin immobilized by electrophoretic transfer onto polyvinylidene membranes (Millipore). The polypeptide complex was separated by SDS-PAGE and transferred to polyvinylidene membranes (Towbin et al., Proc. Natl. Acad. Sci. USA 76:356–375 (1979)). Proteins on the transfer were detected by staining with 1% amido black in methanol: acetic acid::water (20:10:70). The 90 kD T-cadherin peptide band was excised from the membrane and blocked for 30–60 minutes with 4% non-fat dry milk in TBST (10 mM Tris/HCl pH 8.0, 150 mM NaCl and 0.05% Tween 20). The T-cadherin strips were incubated with anti-T-cadherin antiserum (1:50 in TBST) for 2 hours at room temperature. Following washes in TBST, bound anti-T-cadherin antiserum was eluted from the strips with 600 µl 0.1M glycine, pH 2.5 for 5 minutes and neutralized immediately. The procedure was repeated five times to obtain sufficient quantities of purified antibody.

Figure 4:
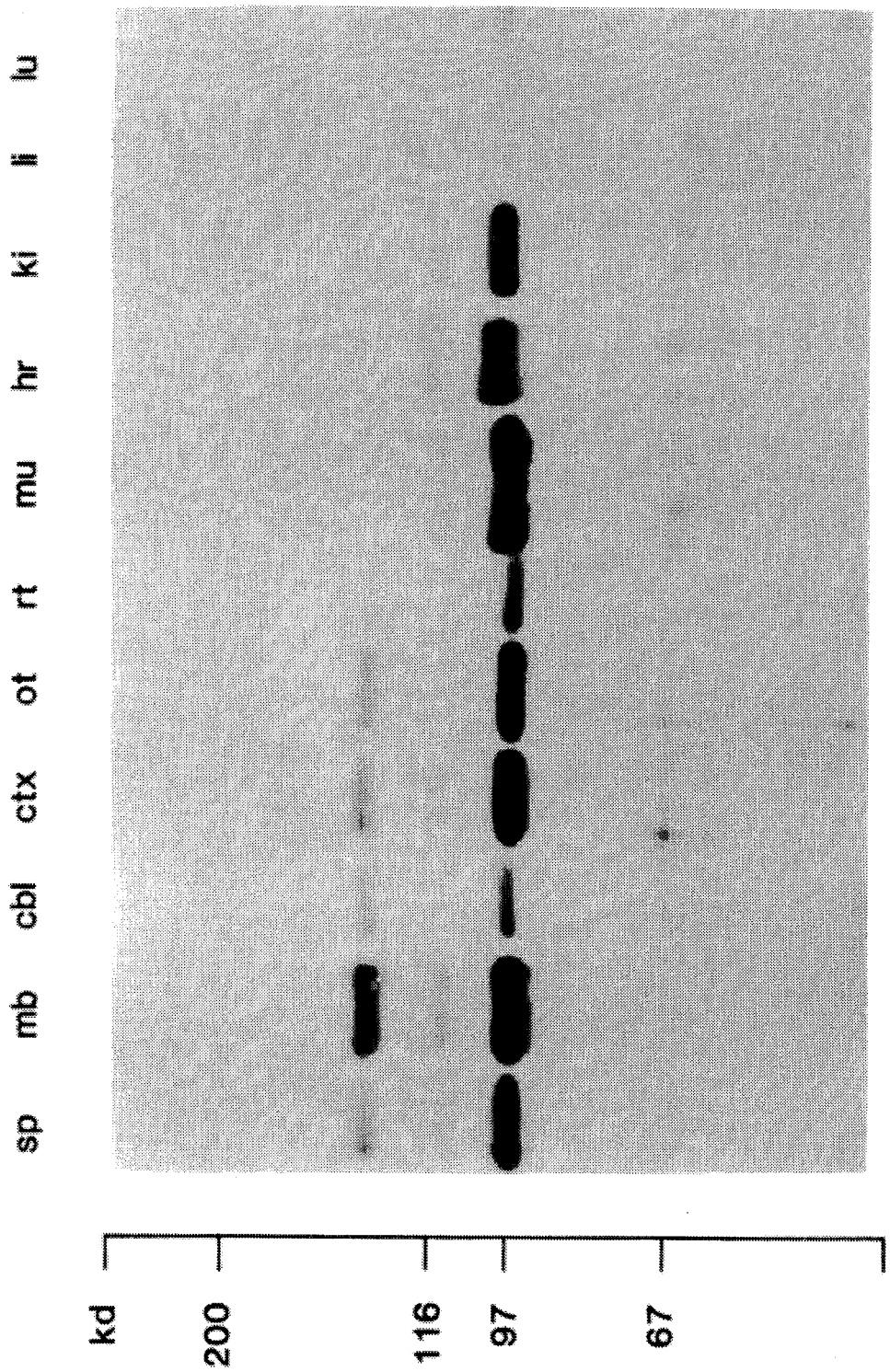
FIG. 4 is an immunoblot of various tissues isolated from 3 day old chicks using antiserum to T-cadherin. Polypeptides having an $M_r$ of 90, 110 and 120 kD are detected in neural tissues whereas only the 90 and 110 kD polypeptides are detected in non-neural tissues. Lane 1, spinal cord; lane 2, midbrain; lane 3, cerebellum; lane 4, cortex; lane 5, optic tectum; lane 6, retina; lane 7, muscle; lane 8, heart; lane 9, kidney; lane 10, liver; lane 11, lung.
Figure 5A:
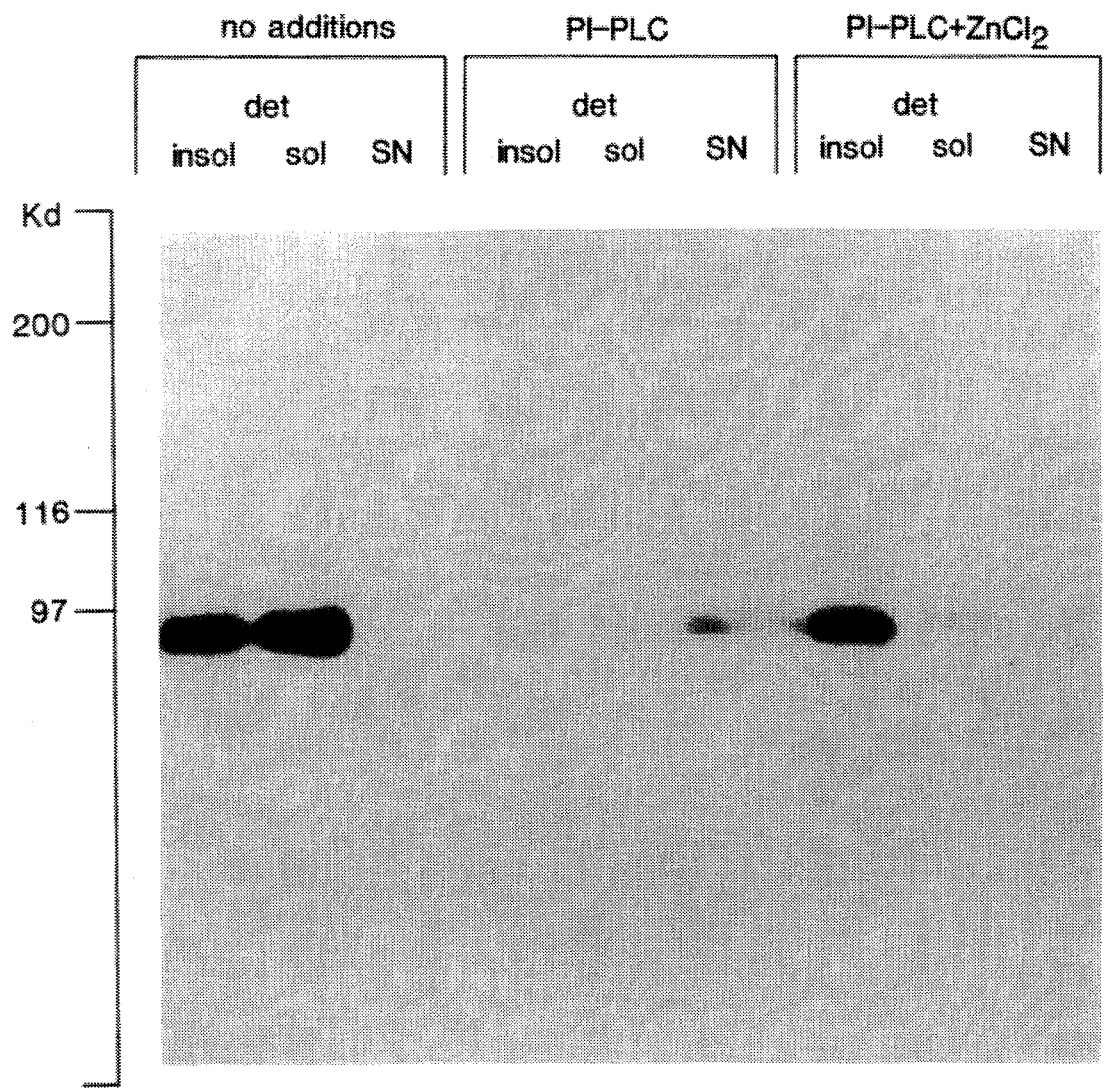
FIG. 5a shows the release of T-cadherin from cultured neurons following phosphotidylinositol phospholipase C (PI-PLC) treatment by Western Blotting with T-cadherin antiserum. T-cadherin is released into the supernatant after PI-PLC treatment (lane 6). The release is blocked by treatment with $ZnCl_2$ (lane 9).
Figure 5B:
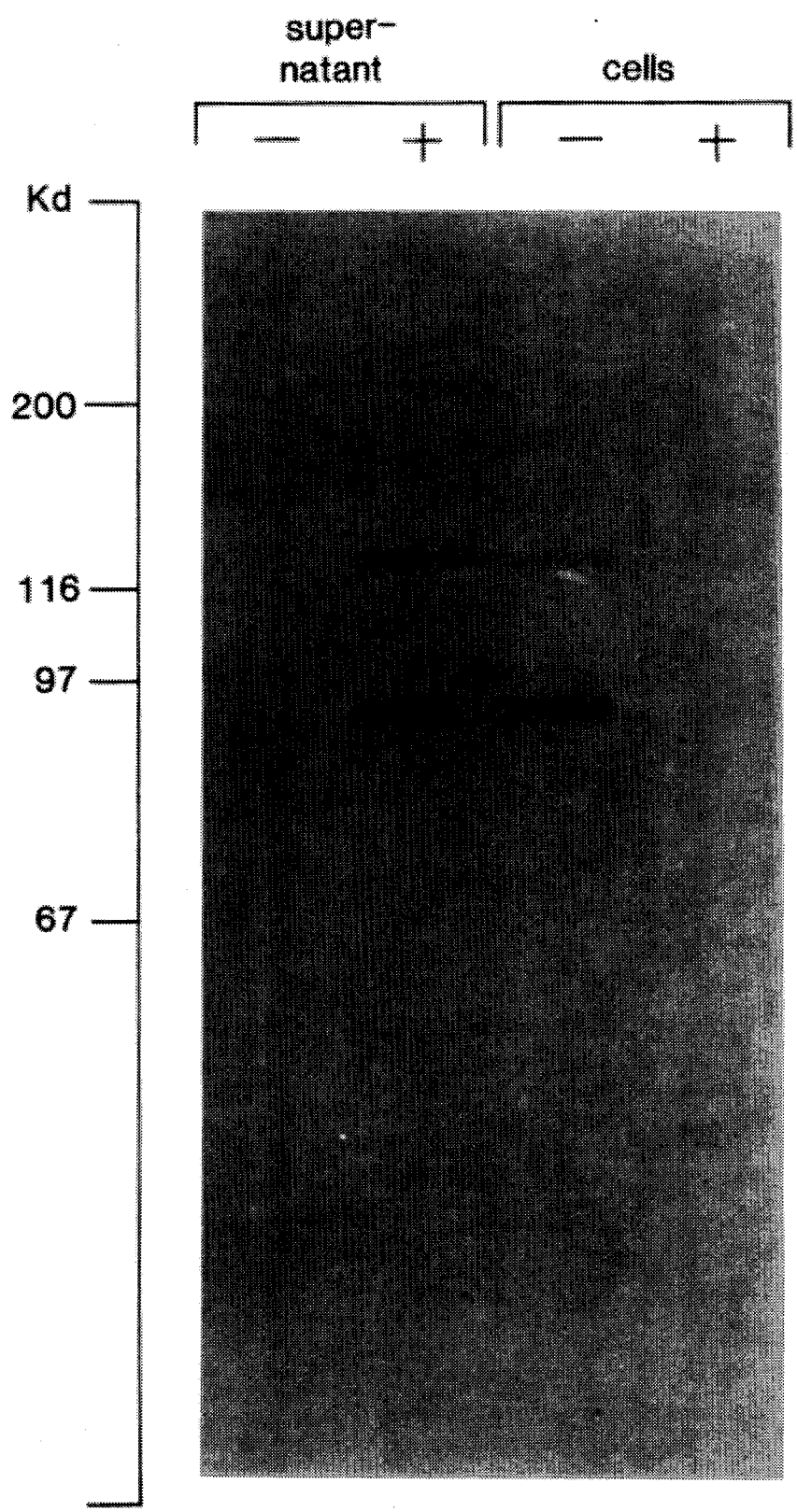
FIG. 5b is an immunoprecipitation of $^3$H-ethanolamine labeled T-cadherin following release from cultured neurons with PI-PLC. Two polypeptides of $M_r$ 90 and 120 kD are released by PI-PLC and are precipitated with T-cadherin antiserum (lane 2).
Figure 6:
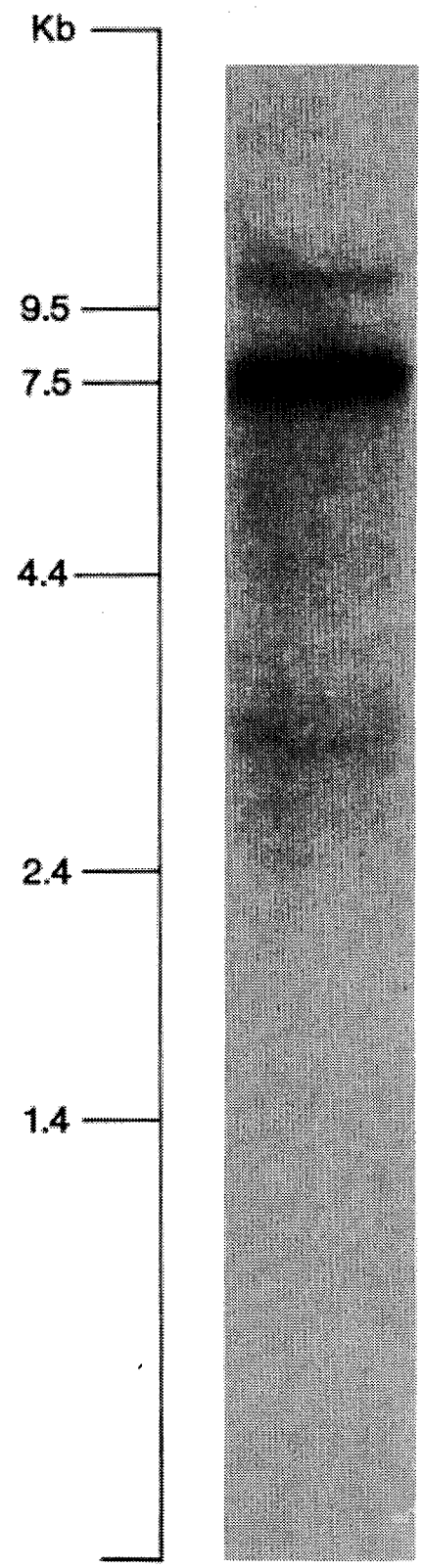
FIG. 6 is an RNA blot of brain tissue probed with a T-cadherin cDNA portion corresponding to the T-cadherin 1 Eco RI-Pst I restriction fragment (1.76 kb). The probe detects two mRNA species of 7.5 and 9.5 kb.

On immunoblots of nervous tissue homogenates, this antiserum recognized a major protein component of 90 kD. In addition, protein species of 110 and 120 kD were detected with the antiserum (FIG. 4). The 110 kD polypeptide is likely to represent T-cadherin with the preptide, since both the 90 and the 110 kD species are obtained after transfection of COS-cells with T-cadherin cDNAs. The 120 kD protein is immunoprecipitated with the T-cadherin antiserum after $^3$H-ethanolamine labelling indicating that this protein is also GPI-linked to the membrane. Therefore, the 120 kD polypeptide is likely to be a nervous system specific form of T-cadherin. In contrast to neural tissue, the T-cadherin antiserum recognizes only the 90 and 110 kD protein species in non-neural tissue samples. Microsequencing of the 17 $NH_2$ terminal amino acids of the 90 kD protein and mapping of this sequence to the protein conceptually translated from the cDNA sequence indicates that the 90 kD protein is a fragment of T-cadherin that starts at amino acid residue 117 (FIGS. 2a, b, c and 2d, e, f) and excludes the signal and the prepeptide.

EXAMPLE IV

Immunoblotting Procedures

Various tissues including brain, retina, muscle, liver, heart and kidney were homogenized in buffer A (see EXAMPLE I) and separated by SDS-PAGE. Separated proteins were electrophoretically transferred to a polyvinylidene difluoride membrane. Marker lanes were stained separately with 0.1% amido black in methanol:acetic acid:$H_2O$ (20:10:70) and destained in the identical solution without the dye. For immunoblotting, non-specific binding sites were blocked as described above and the blots incubated for 60 minutes with anti-T-cadherin antiserum (1:150 for both the non-purified and the purified antiserum). Following washes in TBST, bound antibodies were detected with 1 µCi/ml $^{125}$I goat anti-rabbit immunoglobulin (ICN Biochemicals Inc., Costa Mesa, Calif.) followed by autoradiography using Cronex Lightning Plus screens. In some experiments the blots were reacted using alkaline phosphatase conjugated goat anti-rabbit immunoglobulin and 5-bromo-4-chloro-3-indolylphosphate (BCIP) and nitro blue tetrazolium (NBT) as enzyme substrates (Protoblot, Progema, Madison, Wis.) or the ECL Western Blotting detection system (Amersham Corporation, Arlington Heights, Ill.).

EXAMPLE V

Phospholipase Digestion of Cultured Sympathetic Neurons

Sympathetic ganglia were dissected from 10 day old chicken embryos in L15 medium. The ganglia were dissociated after a 30 minute digestion with 0.25% trypsin in PBS and plated in L15 culture medium onto culture dishes coated with laminin (5 µg/ml, Telios Pharmaceuticals, Inc., La Jolla, Calif.) at a density of $1.4–1.8 \times 10^6$ cells/60 mm culture dish. The culture medium was supplemented with 10% dialyzed fetal calf serum, 0.5% methylcellulose, 2 mM glutamine, 0.6 g/l glucose, nerve growth factor and antibiotics. Extensive nerve fiber growth was observed after a 48-hour culture period.

For phospholipase digestion, 48 hour cultures were extensively washed with PBS. The cultures were incubated for 60 minutes at 37° C. with 5 U/ml phosphoinositol specific phospholipase C (PI-PLC, a gift from Dr. M. Low, Columbia University, N.Y.) in PLC-buffer (PBS containing 1 mM phenylmethylsulfonyl fluoride, 50 µM leupeptin, 5 µM pepstatin, 4 ng/ml aprotinin and 5 µg/ml $\alpha_2$-macroglobulin). The released material was collected, freed of cellular debris by centrifugation and concentrated 10 fold by ultrafiltration. The neuronal cells were peeled off the laminin substrate, washed with PLC-buffer and homogenized in 200 µl H-buffer (10 mM Tris/HCl, pH 7.5, 2 mM $CaCl_2$, 2% Nonidet-P40, 0.25mM dithiothreitol and protease inhibitors phenylmethylsulfonyl fluoride, leupeptin, pepstatin, aprotinin as above). Detergent-soluble and insoluble material was separated by centrifugation at 100,000 g for 45 minutes at 4° C. Control samples received PLC-buffer only; in two experiments 5 mM $ZnCl_2$ was included during the digestion with the phosphoinositol specific phospholipase.

Released and cellular components of the PI-PLC treated cultures were separated by SDS-PAGE and analyzed on Western blots. In control samples (no additions), T-cadherin was found in the detergent soluble and insoluble fraction of the cells. T-cadherin was not detectable in the supernatant after the 60 minute incubation period. In contrast, when cells were treated with PI-PLC, essentially all of the T-cadherin was released into the supernatant after 60 minutes. This release was blocked by $ZnCl_2$ treatment of cells, an inhibitor of PI-PLC.

T-cadherin is secreted into the culture medium over longer culture periods ($\geq 18$ hours). In the culture medium, T-cadherin appears in a highly soluble form as well as in association with an insoluble complex of extracellular matrix components that is pelleted by centrifugation of the culture supernatant at 100,000 g for 3 hours.

EXAMPLE VI

Labeling with $^3$H-Ethanolamine and Fluorography

Cultures of sympathetic neurons were grown for 48 hours and then labeled for 18 hours with $^3$H-ethanolamine (100 µCi/ml; specific activity 19–24 Ci/mmol (Amersham, Arlington Heights, Ill.) in supplemented L15 medium. Labeled cultures were either treated with phosphatidylinositol-specific phospholipase C as described below or processed immediately for analysis. The cells were lysed in H-buffer (10 mMTris/HCl, pH 7.5, 2 mM CaCl$_2$, 2% Nonidet-P40, 0.25 mM dithiothreitol and protease inhibitors: 1 mM phenylmethyl-sulfonyl fluoride, 50 mM leupeptin, 5 µM pepstatin, 4 ng/ml aprotinin) and the proteins separated by SDS-PAGE. Gels were stained with Coomassie Brilliant Blue R250, destained and equilibrated in water. For fluorography processing, the gels were equilibrated in dimethylsulfoxide (DMSO) for 30 minutes and then treated for 60 minutes with 20% 2,5-Diphenyloxazole (PPO) in DMSO. Gels were dried after extensive washing in water and exposed for 4–12 weeks with presensitized Kodak XAR-5 film.

EXAMPLE VII

Immunoprecipitation

T-cadherin was immunoprecipitated from $^3$H-ethanolamine labeled sympathetic neuronal cultures. Following the labeling period, as in EXAMPLE IV, the cultures were thoroughly washed and lysed with 150 mM NaCl in 10 mM Tris/HCl, pH 7.0, 150 mM NaCl, 1% Deoxycholate, 1% Nonident-P40, 0.2% sodium dodecylsulfate, 1 mM phenylmethylsulfonyl fluoride, 50 µM leupeptin, 5 µM pepstatin, 4 µg/ml aprotinin and 1 mM dithiothreitol. The lysate was cleared by centrifugation at 16,000 g for 30 minutes at 4° C. T-cadherin was complexed from the soluble protein pool with anti-T-cadherin antiserum (1:50) for 60 minutes at 4° C. The antigen/antibody complexes were precipitated with fixed staphylococcus aureus (Pansorbin, Calbiochem, La Jolla, Calif.). Precipitates were washed by centrifugation at 3000 g for 20 minutes through layers of 5%, 10% and 20% sucrose. The precipitates were resuspended in SDS-PAGE loading buffer (Maniatis et al., Supra) and analyzed by SDS-PAGE followed by fluorography as described above.

EXAMPLE VIII

Immunocytochemistry

The localization of T-cadherin was examined using indirect immunofluorescence techniques. Chicken embryos between day 2 and 8 of embryonic development were staged using the criteria of Hamburger and Hamilton (J. Morph. 88:49–192 (1951)) (H & H). The animals were fixed by immersion into PLPA-fixative (100 mM Na-periodate, 75 mM lysine and 3% paraformaldehyde in PBS) or 4% paraformaldehyde alone for 1–3 hours depending on their size. The tissue was kryoprotected by successive immersion into 5% and 10% sucrose in PBS for 8–12 hours, embedded in Tissue-Tek (Miles Laboratories Elkhart, Ind.) and frozen at –70° C. Serial sections of 15 µm thickness were cut on a kryostat and collected on gelatine/chromalum (1% gelatine/ 0.4% chromalum) coated slides. Sections were stained for 3–4 hours at room temperature with rabbit anti-T-cadherin (1:100). Bound antibodies were detected with FITC or TRITC conjugated goat anti-rabbit IgG (1:150, Cappel Laboratories, Inc., Westchester, Pa.) Antibody dilutions were in GST-PBS (10% normal goat serum and 0.02% Triton-X100 in PBS), washes after each incubation step with PBS only. Stained sections were mounted with immunomount containing 2% 1,4-Diazabicyclo- (2.2.2)-octane (Aldrich, [Milwaukee, Wis.) to prevent rapid bleaching.

In the developing spinal cord at stage 20 (FIG. 8d) (H & H), motor neurons are in their early phase of differentiation and axon extension. Commissural axons that project from dorsolateral and dorsomedial sites to the floor plate region have commenced to extend processes towards the floor plate that serves as their intermediate target. At this stage of development, T-cadherin was found to be expressed on the cell bodies and nerve fibers of motor neurons and on ventral neuroepithelial cells including the floor plate. Other neurons or their precursors were not stained at this early stage.

At stage 24 (FIG. 8e), the majority of commissural axons have crossed the ventral midline of the spinal cord projecting through the ventral ridge of the floor plate. At this stage, the staining intensity of T-cadherin was strikingly increased in the floor plate region. Comparatively little staining was detected in other areas of the neural tube. The pattern of T-cadherin expression includes the floor plate epithelial cells as in previous stages and a segment of the commissural axons as they cross this area. This pattern suggests that commissural axons are stained by anti-T-cadherin only in the segment in contact with the floor plate. The expression in the floor plate region was transient, since in older animals little staining or none can be detected in the floor plate area.

Figure 8A:
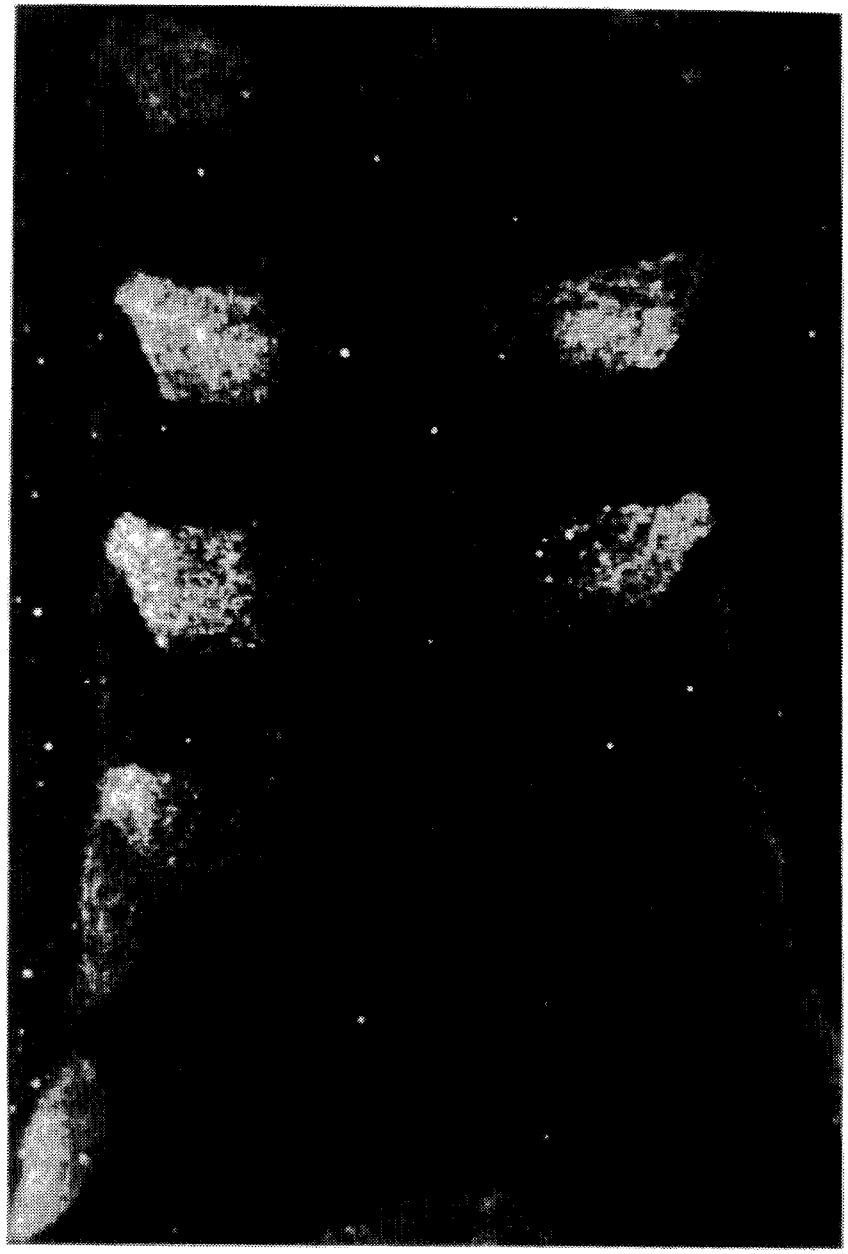
FIG. 8 is an immunohistochemistry analysis of T-cadherin expression in the developing nervous system. The tissues examined are: (a,b,c) somites H/H stage 23; (d,e,f) developing spinal cord, panel 1, H/H stage 20, panel 2, H/H stage 24 and panel 3, H/H stage 32; (g) blood vessel; and (h) muscle.
Figure 8C:
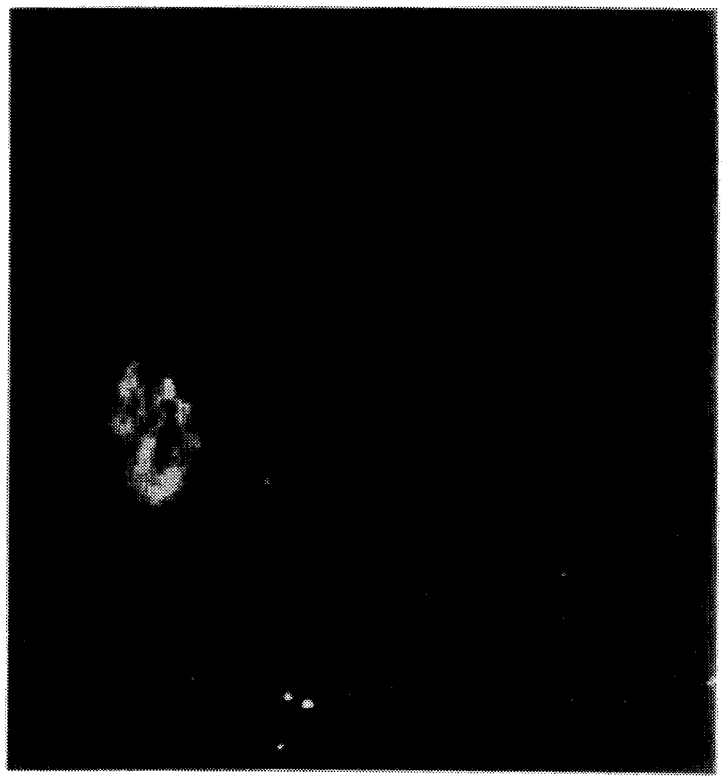
Figure 8B:
Figure 8G:
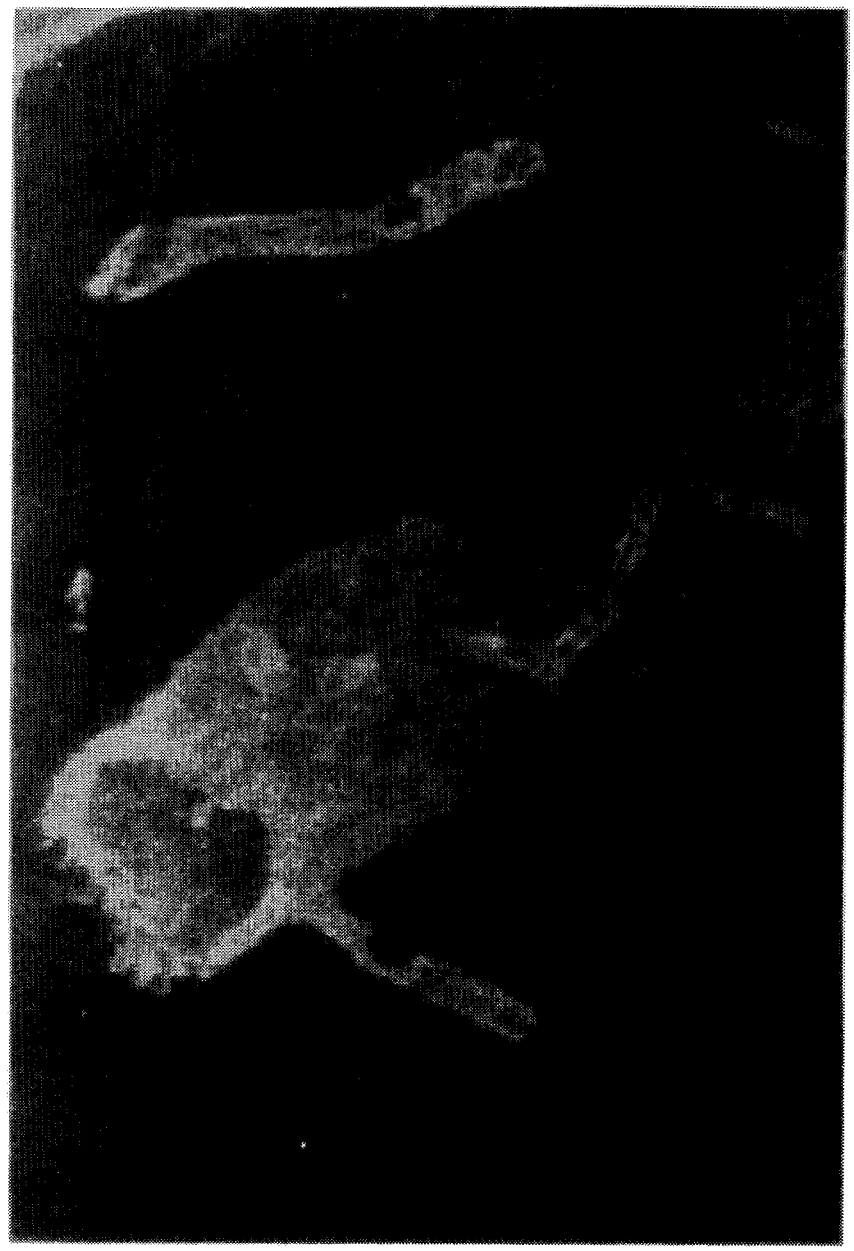
Figure 8H:

Motor neurons select as their intermediate targets the anterior region of the somitic sclerotome (Keynes and Stern, Nature 310:786–789 (1984)), thus establishing a segmental pattern of nerve projections. In coronal sections of stage 22–23 chicken embryos, T-cadherin was expressed in a striking segmental pattern on the surface of posterior somite cells (FIG. 8a). The spinal nerve fascicles crossing the anterior somite regions were identified in an adjacent section with anti-contactin antibodies (FIG. 8c). The segmental pattern of T-cadherin expression was observed as early as neural crest cells enter the somite regions.

EXAMPLE IX

Identification of cDNA Clones Encoding T-cadherin

A cDNA library generated from embryonic day 13 chicken brain (Ranscht, J. Cell Biol. 107:1561–1573 (1988)) was screened for cDNA clones encoding T-cadherin. Nitrocellulose replica filters of a lambda gt 11 expression library from embryonal day 13 chick brain were screened with affinity purified anti-T-cadherin antiserum (1:40). Screening was essentially as described by Maniatis, incorporated herein by reference. Alkaline phosphatase conjugated goat anti-rabbit immunoglobulin and 5-bromo-4-chloro-3-indolyl phosphate (BCIP) and nitro blue tetrazolium (NBT) substrates (Protoblot, Progema) were used as a detection system. In the initial screening one clone was isolated from 7×10$^5$ amplified and 8×10$^4$ unamplified recombinants. This clone represented a true T-cadherin transcript by two criteria:

1) The cDNA encoded a fusion protein that was recognized by anti-T-cadherin antiserum. Affinity purification of the antiserum on recombinant fusion protein selected antibodies specific for the 90 kd protein in brain homogenates on Western blots. Moreover, the affinity purified antiserum stained in indirect immunofluorescence on sections of stage 22–23 chick embryos posterior somite segments.

2) Conclusive evidence that the selected cDNA represented a T-cadherin transcript was obtained by comparison of the conceptually translated cDNA sequence with the amino acid sequence obtained by microsequencing of the NH$_2$-terminus of the 90 kD protein. The 17 NH$_2$-terminal amino acids of the 90 kD polypeptide mapped to amino acids 117 to 133 in the open reading frame of the protein conceptually translated from the cDNA sequence (See FIGS. 2a, b, c and 2d, e, f).

EXAMPLE X

Isolation of Additional T-cadherin cDNA Clones

Sixteen additional cDNA clones for T-cadherin were isolated by screening both lambda gt 10 (amplified) and lambda gt 11 (unamplified) chick brain libraries with T-cad-2 restriction fragments that were labeled by nick translation (Maniatis et al., Supra; kit from Bethesda Research Laboratories [Gaithersburg, Md.]). The restriction fragments constituted nucleotides 440–1559 of the initially isolated clone and included the coding sequences encoding the NH$_2$-terminus of the 90 kD protein. Phage plaques were transferred in duplex to Hybond nylon membranes (Amersham, Arlington Heights, Ill.). The filters were processed successively through 1.5M NaCl/0.5M NaOH for 2 minutes, 3M Na-acetate, pH 5.2 for 5 minutes and 20×SSPE (3M NaCl, 0.2M NaH$_2$PO$_4$×H$_2$O, 0.02 M Na$_2$ EDTA, pH 7.4), dried and baked for 60 minutes in a vacuum oven. Prehybridization was at 42° C. in 50% deionized formamide, 5×SSPE, 1× Denhardts and 100 µg/ml salmon sperm DNA for 2–4 hours. Hybridization was overnight under identical conditions with the probe at 2×10$^6$ cpm/filter. The filters were washed under high stringency conditions (0.2×SSPE/0.2% SDS at 68° C.) and exposed overnight to Kodak XAR-5 film.

All clones shared restriction sites within their internal nucleotide sequence, but varied in length from 1 to 3.8 kb. EcoR1 restriction fragments of all clones were subcloned into the Bluescript KS+ vector (Stratagene, La Jolla, Calif.) and used for nucleotide sequence determination using a double stranded DNA as a template. Sequence over internal EcoR1 sites was obtained from lambda cDNA templates. The nucleotide sequence of clone 266 (=T-cad 1), one of the longest cDNA clones (3.8 kb) and of cDNA 1212 (=T-cad 2) are shown in FIGS. 2a, b, c and 2d, e.

EXAMPLE XI

RNA Isolation

Total cellular RNA was isolated from hatched chicks by the guanidinium isothiocyanate method (Maniatis et al., Supra). Briefly, the tissues were homogenized on ice in 4 to 6 mls of 4M guanidinium thiocyanate (GTC) buffer per gram of tissue (94.4 g GTC, 1.67 ml 3M sodium acetate, pH 6.0, 0.5% sarkosyl, 200 µl antifoam A, 500 µl 1 NaOH, to 200 ml with DEPC treated dd H$_2$O, 0.1M final concentration of 2-mercaptoethanol should be added just prior to use). The homogenate is layered onto 4 to 5 mls of 5.7 M CsCl solution in a SW 40 centrifuge tube (Beckman, Carlsbad, Calif.). The CsCl solution is prepared in the following manner: 95.97 g CsCl, 0.83 mls 3M sodium acetate pH 6.0, to 100 mls with DEPC-dd H$_2$O and filter sterilize. The tubes are balanced with GTC buffer and the samples are centrifuged at 32,000 rpm for 18 hours using an ultracentrifuge (Sorvall, Newtown, Conn.). Following centrifugation, the GTC buffer and CsCl solution is aspirated off leaving about 1 ml of CsCl solution covering the RNA pellet. The walls of the tube are rinsed with 1 to 2 mls of GTC buffer and the buffer, including CsCl layer, is carefully removed. The tubes are cut 1–2 cm from the bottom using a hot razor blade and the RNA pellets are rinsed with 400 µl of 20° C. ethanol, dried and resuspended in Tris-EDTA (TE; 10 mMTris-Hcl, pH 7.6, 1 mM EDTA). The resuspended RNA is purified by extracting twice with an equal volume of phenol/chloroform followed by ethanol precipitation and washing as described above. RNA was quantitated by absorbance at 260 nm (OD$_{260}$ of 1=50 ml/ml). Purity was checked by determining the absorbance ratio at 260 nm compared to the absorbance at 280 nm (OD 260/280≧2.0 for RNA). The RNA samples were stored as ethanol precipitates at 70° C. until further use. From tissues of early developing chicken embryos, RNA was prepared by lithium precipitation as described in Maniatis, Supra. When probed with T-cadherin cDNA, two transcripts of approximately 9.5 and 7.5 kb were detected.

EXAMPLE XII

RNase Protection

RNA transcripts encoding the T-cadherin prepeptide and 3' untranslated regions were generated by in vitro transcription of T-cadherin cDNA. The template for the prepeptide probe (common to T-cad 1 and T-cad 2) was a 274 bp EcoR1 restriction fragment (FIGS. 2d, e, f) from lambda gt 11 T-cad 2 cloned into Bluescript KS$^+$. The fragment was linearized by digestion with HindIII in the polylinker region. A specific 3' end probe of T-cad 1 was generated by removing 1.5 kb untranslated sequence from the extreme 3' end of clone T-cad 1 by restriction digestion with StuI/SmaI and religation of the blunt ends. A 168 bp template was obtained by linearizing T-cad 1 DNA with SfaI. A specific 3' end template for T-cad 2 was generated by cloning its 2.1 kb EcoR1 restriction fragment into Bluescript KS$^+$ and digestion of the cDNA fragment with Hpa1. Chicken β-actin cDNA (kindly provided by Dr. D. Cleveland, Johns Hopkins University, Baltimore, Md.) was used as a control. The β-actin cDNA was digested with KpnI and HindIII and cloned into the SP72 transcription vector (Melton et al., Nucleic Acids Res. 13:7035–7056 (1984)). The DNA was linearized by digestion with PvuII. The templates were transcribed in anti-sense orientation in the presence of T7 RNA polymerase and $^{32}$P-rUTP under conditions described by Melton, Supra. Probes were purified on polyacrylamide gels. A 1% aliquot of the total probe was hybridized overnight in 80% formamide, 400 mM NaCl, 4 mM PIPES and 1 mM EDTA at 45° C. to 2–10 µg total RNA from various tissues. Non-hybridized RNA was digested with RNases A and T1 for 60 minutes at room temperature. RNA hybrids were separated on polyacrylamide gels and analyzed after exposure to Kodak XAR-5 film.

All tissues that show a protected fragment with the prepeptide probe, also showed a protected fragment with the 3' fragment, indicating that mRNA encoding the phosphoinositol linked form of T-cadherin exists in the tissues. Brain, heart, retina, cultured sympathetic neurons, stage 37 and 24 spinal cord (especially floor plate), and somites revealed protected fragments.

Although the invention has been described with reference to the presently preferred embodiment, it should be understood that various modifications can be made without departing from the spirit of the invention. Accordingly, the invention is limited only by the following claims.

I claim:

1. A substantially purified polypeptide designated T-cadherin wherein said polypeptide is a cadherin cell adhesion molecule anchored to cell plasma membranes through a glycosyl phosphatidylinositol linkage;

said polypeptide having an amino acid sequence set forth in FIGS. 2a, b, c or 2d, e, f;

and wherein said polypeptide is cross-reactive with antibodies reactive against polypeptides having the amino acid sequences set forth in FIGS. 2a and 2b, but not reactive with the antibodies reactive against N-cadherin, E-cadherin, P-cadherin, or L-CAM.

2. The substantially purified polypeptide of claim 1 designated as T-cad 1 having the amino acid sequence set forth in FIGS. 2a, b, c.

3. The substantially purified polypeptide of claim 1 designated as T-cad 2 having the amino acid sequence set forth in FIGS 2d, e, f.

4. The polypeptide of claim 1 wherein said polypeptide is produced recombinantly.

* * * * *

UNITED STATES PATENT AND TRADEMARK OFFICE
CERTIFICATE OF CORRECTION

PATENT NO.    : 5,585,351
DATED         : December 17, 1996
INVENTOR(S)   : Barbara Ranscht Page 1 of 1

It is certified that error appears in the above-identified patent and that said Letters Patent is hereby corrected as shown below:

Column 12,
Line 2, please delete "20°" and replace therefor -- -20° --.
Line 11, please delete "70°" and replace therefor -- -70° --.

Signed and Sealed this

Sixteenth Day of October, 2001

Attest:

*Nicholas P. Godici*

NICHOLAS P. GODICI
*Acting Director of the United States Patent and Trademark Office*

*Attesting Officer*